(12) United States Patent
Borges et al.

(10) Patent No.: US 12,283,770 B2
(45) Date of Patent: Apr. 22, 2025

(54) METHOD AND SYSTEM FOR MODULAR CONNECTIONS WITH ELECTRICAL COMPONENTS

(71) Applicant: CareFusion 303, Inc., San Diego, CA (US)

(72) Inventors: Gregory Borges, San Diego, CA (US); Daniel Govea, San Diego, CA (US); Roman Dodge, Santee, CA (US); Daniel Kimm, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/344,105

(22) Filed: Jun. 29, 2023

(65) Prior Publication Data

US 2023/0344168 A1    Oct. 26, 2023

Related U.S. Application Data

(63) Continuation of application No. 18/070,226, filed on Nov. 28, 2022, now Pat. No. 11,764,517, which is a
(Continued)

(51) Int. Cl.
H01R 13/627    (2006.01)
A61B 1/00      (2006.01)
A61M 5/14      (2006.01)

(52) U.S. Cl.
CPC ..... H01R 13/6271 (2013.01); A61B 1/00124 (2013.01); A61M 5/1413 (2013.01)

(58) Field of Classification Search
None
See application file for complete search history.

(56) References Cited

U.S. PATENT DOCUMENTS 3,513,434 A * 5/1970 Zielke ............... H01R 4/4863
                                                439/840
4,753,604 A * 6/1988 Wheeler ............ H01R 13/523
                                                439/271
(Continued)

FOREIGN PATENT DOCUMENTS

| EP | 0843563 A1 | 5/1998 |
| EP | 1532995 A1 | 5/2005 |
| WO | WO-9856450 A1 | 12/1998 |

OTHER PUBLICATIONS

Canadian Office Action for Application No. 3,165,140, dated May 30, 2024, 4 pages.
(Continued)

*Primary Examiner* — Tho D Ta
(74) *Attorney, Agent, or Firm* — Morgan, Lewis & Bockius LLP

(57) ABSTRACT

An electronic module for a modular patient care system is disclosed. The electronic module can include a housing having an attachment side configured to releasably attach to an adjacent electronic module. A latch mechanism can be configured to engage a catch member on the adjacent electronic module to secure the attachment side to the adjacent electronic module. An electrical connector positioned on the attachment side can be configured to electrically connect to an adjacent electrical connector on the adjacent electronic module. A sensor coupled to the housing can be configured to detect movement of the latch mechanism indicative of at least one of engagement or disengagement of the latch mechanism from the adjacent electronic module.

19 Claims, 21 Drawing Sheets

Related U.S. Application Data continuation of application No. 17/152,627, filed on Jan. 19, 2021, now Pat. No. 11,515,667.

(60) Provisional application No. 62/963,963, filed on Jan. 21, 2020.

(56) References Cited

U.S. PATENT DOCUMENTS

| | | | | |
|---|---|---|---|---|
| 5,007,842 | A | * | 4/1991 | Deak .................. H01R 12/714 439/493 |
| 5,030,109 | A | * | 7/1991 | Dery ................... H01R 12/714 439/840 |
| 5,273,438 | A | * | 12/1993 | Bradley ............. G01R 1/07307 439/591 |
| 5,535,512 | A | * | 7/1996 | Armogan ........... H01R 13/5202 29/877 |
| 5,836,910 | A | | 11/1998 | Duffy et al. |
| 5,941,846 | A | | 8/1999 | Duffy et al. |
| 6,381,146 | B1 | | 4/2002 | Sevier |
| 6,851,985 | B2 | | 2/2005 | Lafragette et al. |
| 7,074,205 | B1 | | 7/2006 | Duffy et al. |
| 9,905,960 | B2 | * | 2/2018 | Liang .................. H01R 13/405 |
| 11,515,667 | B2 | | 11/2022 | Borges et al. |
| 2008/0079224 | A1 | | 4/2008 | Thoms et al. |
| 2012/0004602 | A1 | | 1/2012 | Hanson et al. |

OTHER PUBLICATIONS

International Search Report and Written Opinion for Application No. PCT/US2021/014007, dated Jun. 7, 2021, 20 pages.

Invitation to Pay Additional Fees, Partial International Search Report, and Provisional Opinion for Application No. PCT/US2021/014007, dated Apr. 13, 2021, 13 pages.

European Partial Search Report for Application No. 24190795.5, dated Oct. 14, 2024, 12 pages.

Extended European Search Report for Application No. 24190795.5, dated Jan. 10, 2025, 12 pages.

* cited by examiner

METHOD AND SYSTEM FOR MODULAR CONNECTIONS WITH ELECTRICAL COMPONENTS This application is a continuation of U.S. application Ser. No. 18/070,226 filed Nov. 28, 2022, which is a continuation of U.S. application Ser. No. 17/152,627 filed Jan. 19, 2021, now U.S. Pat. No. 11,515,667 issued Nov. 29, 2022, which claims the benefit of priority to U.S. Provisional Application No. 62/963,963 filed on Jan. 21, 2020, the entirety of each is incorporated herein by reference.

BACKGROUND

Modular patient care systems can provide versatility and flexibility for treatment or monitoring of patients across various patient care areas. Such systems can employ multiple modules mechanically and electrically coupled together using releasable attachments that permit customization and allow for exchange of power or data between coupled modules.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 1A illustrates a front view of the system in a configuration having an interface module attached to a functional module, and FIG. 1B illustrates a rear view of the system in a configuration having the interface module without the functional module attached.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Modular patient care systems can present a safety risk where, for example, the modules are improperly secured or inadvertently bumped, which can cause operation or patient care to be interrupted. These systems may also employ high currents or operate in environments exposed to therapeutic or bodily fluids, which presents a risk of damage to electrical connection interfaces due to moisture or electrical arcing between modules.

Figure 1A:
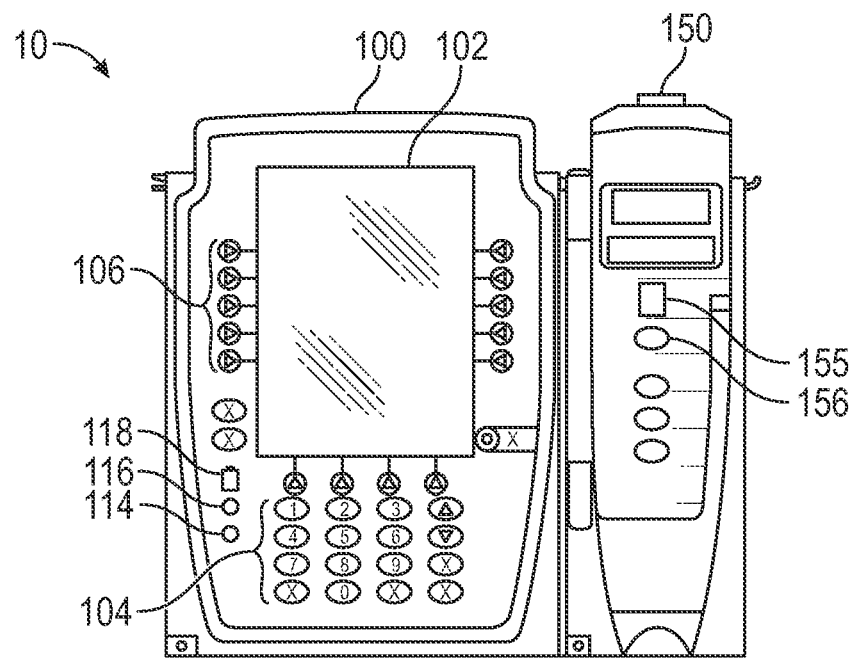
FIGS. 1A-1B illustrate a modular patient care system, in accordance with some embodiments.
Figure 1B:
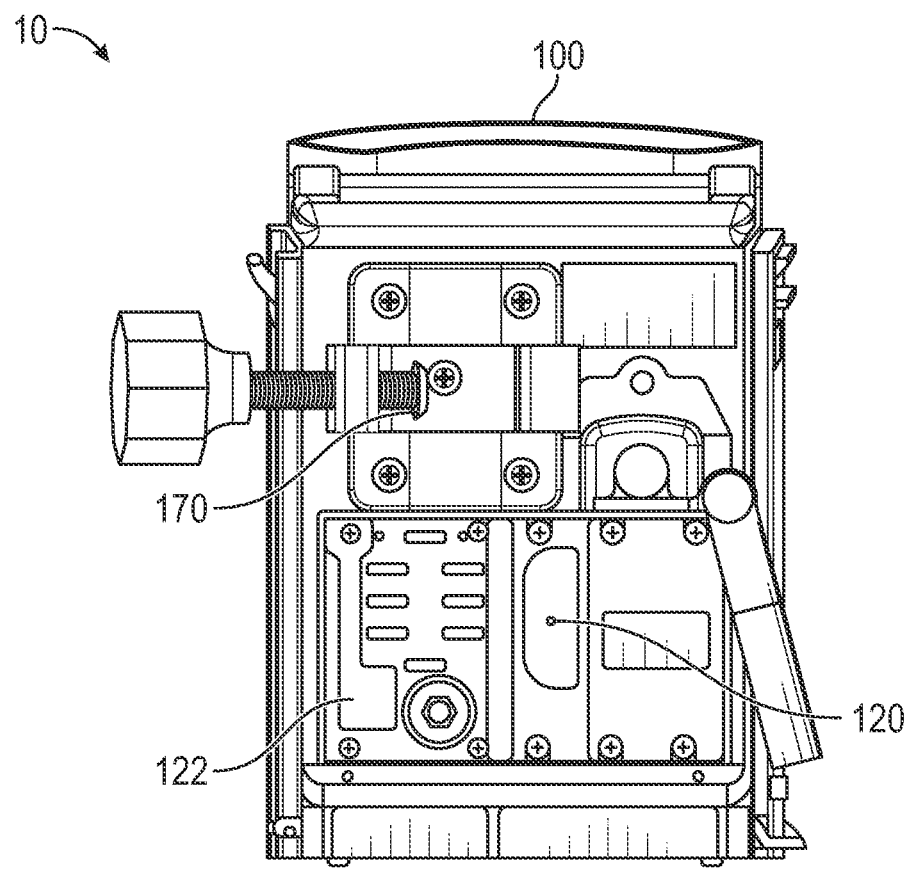

FIGS. 1A-1B show an example of a modular patient care system 10, in accordance with some embodiments. FIG. 1A shows a front view of the modular patient care system 10 including an interface module 100 and a functional module 150 in an attached configuration, while FIG. 1B shows a rear view of the modular patient care system 10 with only the interface module 100 in a detached configuration.

The modular patient care system 10 is an example of a modular system that can employ any of the attachment technologies further described herein in connection with other figures. The modular patient care system 10 includes a plurality of modules or units, such as an interface module 100 and one or more of the functional modules 150, which may be releasably or detachably coupled together.

Interface module 100 can be configured to perform any one or more of the following functions in the patient care system 10: (i) it can provide a physical base of the system that attaches to structures such as intravenous (IV) poles or bed rails; (ii) it can provide power to components of the system such as, for example, the functional module(s) 150; (iii) it can provide an interface between the system and external devices, and/or (iv) it can provide a primary or centralized user interface of the system. Interface module 100 can include input/output (I/O) devices that can be configured for interaction with a user. The I/O devices shown in FIG. 1A include a display device 102 and buttons, including hard keys 104 and soft keys 106. While a display and buttons are shown, it is contemplated that the modular patient care system 10 or any module thereof can include or be coupled to any suitable I/O devices to permit user observation or control, such as, for example, one or more speakers, microphones, motion sensors, touch sensors, pointing devices, or depth sensors.

Display device 102 may be implemented as any suitable type of information display, such as, for example, a liquid crystal display (LCD), an organic light-emitting diode (OLED) display, or a micro-LED display. Display device 102 may be configured to be used during setup and operating procedures to facilitate data entry and editing. Display device 102 may also be used to display various operating parameters, such as volume to be infused (VTBI) for individual functional modules 150, current time of day, prompts, advisories, and/or alarm conditions.

As noted, interface module 100 is shown with a plurality of hard keys 104 and soft keys 106, which can be used for entering data and commands. The numerical hard keys 104 can be configured to enter numerical data, while remaining keys of the hard keys 104, as well as the soft keys 106, can be configured to enter operational commands. Soft keys 106 are shown arranged along the edges of the display device 102 so as to interact with information presented on the display device 102 to define the function of a particular soft key 106 at any given time. Accordingly, a particular soft key 106 when pressed can allow for the selection of an option, or an infusion or monitoring parameter, which is displayed on the display device 102 adjacent to the particular soft key. As noted, hard keys 104 may also be used for entering specific operational commands. For example, particular hard keys when pressed can be respectively configured to cause the system to change from standby mode to an operating mode, to temporarily disable audio functionality of interface module 100, or to allow a user access to available system or functional module options, among other possible commands.

As shown in FIG. 1A, interface module 100 can also include one or more indicators for providing indications of various conditions of the module or other information. In FIG. 1, interface module 100 is shown with three indicators, including a communication indicator 114, an external power indicator 116, and an internal power indicator 118. Communication indicator 114 may be configured to indicate that the system is communicating with a compatible external computer system. External power indicator 116 may be configured to indicate that interface module 100 is connected to and operating with an external power source. Internal power indicator 118 may be configured to indicate that the interface module 100 is operating with the use of an internal power source (e.g., a battery). Each of the indicators may, for example, include a light source such as a light emitting diode (LED) that is configured to illuminate to provide the respective indication when the corresponding condition is present.

The modular patient care system 10 may also include one or more external communication interfaces 120. In the example shown in FIG. 1B, a communication interface 120 is located at the rear of interface module 100. Communication interface 120 can be, for example, an industry standard wireless network memory card or a personal computer memory card international association (PCMCIA) slot for receiving PCMCIA cards, although one skilled in the art could select from a variety of commercially available communication protocols or industry standards. The modular patient care system 10 may also include one or more interface ports 122. In the example shown in FIG. 1B, interface port 122 is located at the rear of interface module 100. The interface port 122 can include, for example, industry standard RS-232 ports and/or RJ45 ports, although again, one skilled in the art could select from a variety of commercially available communication protocols or industry standards. Further, although the example shown in FIGS. 1A-1B is described as containing communication interface 120 and interface port 122, any number or combination of communication interfaces and/or ports could be included in various embodiments of the interface module 100.

Communication interface 120 and/or interface ports 122 may, for example, be used to download drug libraries, drug delivery profiles, other system configuration values, and/or may be used to upload event history data from interface module 100. Additionally or alternatively, communication interface 120 and/or interface port 122 may act as an interface to patient monitoring networks and nurse call systems, or as an interface to external equipment such as barcode readers to provide a means of inputting drug and/or patient information from medication or patient records. In some embodiments, interface ports 122 and/or communication interface 120 may be supplemented with one or more peripheral device ports, such as a Patient Controlled Analgesia (PCA) port. The PCA port can provide a connection to a remote hand-held dose request button, which can be used by a patient to request a medication dose during PCA applications.

As seen in FIG. 1B, interface module 100 can also include a clamp 170 for use in attaching interface module 100 to a structure such as an IV stand or a hospital bed. In the example shown in FIG. 1B, the clamp 170 is positioned on a rear surface of the interface module 100. The clamp 170 may be any clamp suitable for attaching bedside patient monitoring or infusion apparatus to these structures.

Also shown in FIG. 1A is a functional module 150. It is to be understood that although only a single functional module 150 is shown in FIG. 1A, the modular patient care system 10 can be configured so that any number of functional modules 150 may be connected using modular attachment mechanisms described herein, and in any order to either or both sides of interface module 100. The type and number of functional modules 150 attached to interface module 100 may be any suitable number based on the physical and electric ability of the wiring and of the interface module to handle the desired types and numbers of functional modules. Functional module 150 may be selected from a wide variety of functional devices, including those for patient therapies and/or patient monitoring. For example, functional module 150 may be an infusion pumping module, a PCA module, a syringe pump module, a pulse oximetry module, an invasive or non-invasive blood pressure monitor module, an electrocardiograph module, a bar code or identification (ID) code reader module, a printer module, a temperature monitor module, a radiofrequency (RF) telemetry link module, a fluid warmer/IV pump module, or a high rate IV pump module (e.g., 2000+ ml/hr). It is also contemplated that the functional module 150 could be adapted for other uses.

Each functional module 150 can include a channel position indicator 155, which identifies the position of the functional module within the modular patient care system 10. By way of example, the modular patient care system 10 may include four channel positions, A, B, C, and D. When four functional modules are attached in the system, the functional modules can each respectively be in one of the four channel positions A, B, C, and D, and the channel position indicator 155 on each individual functional module can visually indicate the corresponding channel position. The channel positions can be designated A-D, beginning with the first module on the left. The positions of each functional module with respect to each other or with respect to the interface module 100 may be interchanged, but the channel locations A-D may stay in the same positions.

Figure 2:
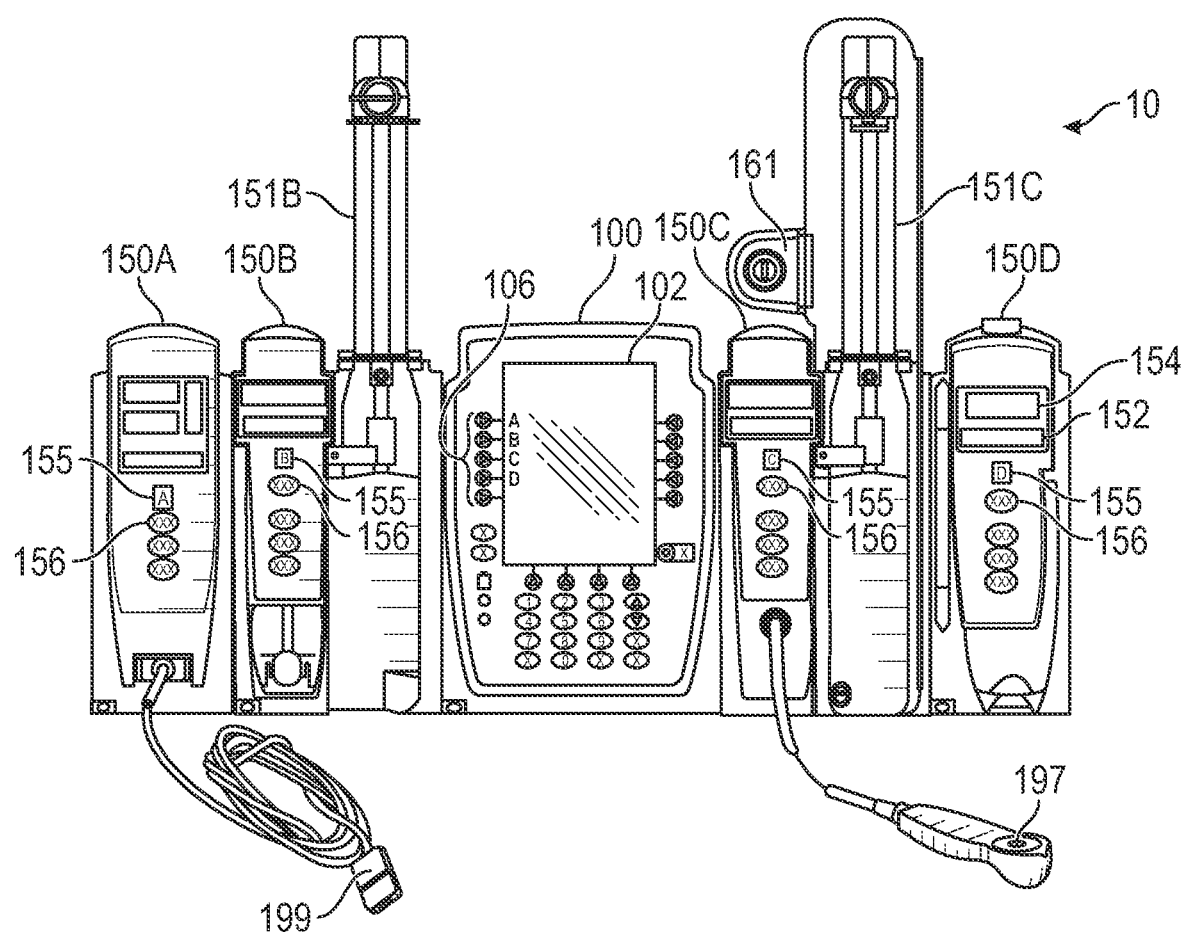
FIG. 2 illustrates a front view of a modular patient care system in a configuration having an interface module attached to four functional modules, in accordance with some embodiments.

FIG. 2 illustrates an example with four functional modules attached to interface module 100, in accordance with some embodiments. Regardless of which module is placed immediately to the left of interface module 100, that module can always indicate channel position B on the channel position indicator 155. The functional modules may each further contain certain function specific information, which is communicated to interface module 100 to indicate what type of functional module is at each channel position. Each functional module 150 may also have one or more buttons, such as a select key 156, which permits selection of the module.

In the example shown in FIG. 2, the modular patient care system 10 includes four different functional modules, including a pulse oximetry module 150A at position A, a syringe pump module 150B at position B, a PCA module 150C at position C, and an infusion pump module 150D at position D. The respective position of each functional module is indicated on the functional module at indicator 155. Because four functional modules are in use, display device 102 on interface module 100 indicates A through D. The system can be configured to allow selection of a functional module to perform a particular function or procedure through interface module 100 by depressing the appropriate soft key 106 adjacent to the desired, indicated channel and functional module. Additionally or alternatively, the system can be designed such that selection of a particular functional module is accomplished by pressing the select key 156 located on the desired functional module in order to select that functional module. When the desired functional module is selected, display device 102 of the interface module 100 can be configured so as to act as the user interface for the selected functional module. For example, display device 102 can be configured in accordance with a function specific domain to provide function specific displays and soft keys based on the selected functional module.

Infusion pump module 150D shown in FIG. 2 is a pumping device for basic fluid infusion. Infusion pump module 150D can include a control system to control the various functions performed by such a pump, including the control of fluid delivery to the patient and the monitoring of the fluid path for occlusion or air-in-line. In the example shown, infusion pump module 150D includes two display devices, including a rate display 154 that may be used to display the actual infusion rate at which the pump is operating, and a channel message display 152 that may be used to display informational, advisory, alarm, or malfunction messages.

The infusion pump control may also contain input devices such as hard keys for data and command entry. Select key 156 of the infusion pump module 150D may be implemented as a hard key, and may be configured to allow the user to select a channel for infusion parameter entry. Other input devices such as other hard keys when pressed may, for example, be configured to pause an infusion while the infusion is occurring, be configured to resume operation of a previously paused infusion, or be configured to stop the infusion occurring on the channel, deselect the channel, and if the functional module on the channel has been the only functional module operating, power off the system. Infusion pump module 150D may contain one or more indicators, which illustratively illuminate when the functional module is in alarm or infusion complete condition, when the functional module is programmed for a future start time or has been paused, or when the functional module is performing an infusion. Other appropriate indicators may be included in other functional modules.

Also shown in FIG. 2 is pulse oximetry module 150A, syringe pump module 150B, and PCA module 150C. As shown, pulse oximetry module 150A, syringe pump module 150B, and PCA module 150C each contain a set of buttons such as hard keys like those found on infusion pump module 150D. Pulse oximetry module 150A is a pulse oximetry device, and it includes or is coupled to a peripheral device containing a pulse oximetry sensor 199 that can couple directly to a patient to measure the oxygenation in the patient's blood. Syringe pump module 150B is a pumping device for precision fluid delivery, and can contain a syringe along with a syringe pusher for manually infusing fluids. For example, syringe pump module 150B is shown with a syringe receptacle 151B that is configured to receive a syringe therein. PCA module 150C is a drug delivery device, and it includes or is coupled to a peripheral device containing a dose request button 197 that can be pressed directly by a patient to request a dosage of medication or trigger delivery of a dosage of analgesia. PCA module 150C can also include a door lock 161 for providing security for enclosed narcotics or other matter to be infused. PCA module 150C is also shown with a syringe receptacle 151C configured to receive a syringe therein. In addition, pulse oximetry module 150A, syringe pump module 150B, and PCA module 150C each include one or more displays and one or more indicators which may be used to present appropriate information.

In modular systems such as the modular patient care system 10, releasable or detachable modular attachment mechanisms can be employed to allow for customization or reconfiguration during use, while provide electrical and mechanical connections when modules are attached. In the example shown in FIGS. 1A-2, electrical connectors and latch mechanisms can be located on opposing sides of each module, including interface module 100 and each functional module. Such mechanisms can be used to directly attach any functional module to the interface module, or directly attach any functional module to any other functional module, in a linear arrangement in which the modules are stacked side by side in a row. These attachment mechanisms can provide physical support for the attached functional modules and also provide power and internal communication connections between the interface module 100 and the functional modules. The attachment mechanisms can be made identical to each other across different modules so that each module can be capable of mating with another module. Optionally, some attachment mechanisms may prevent inadvertent connections between two interface modules 100.

Figure 3:
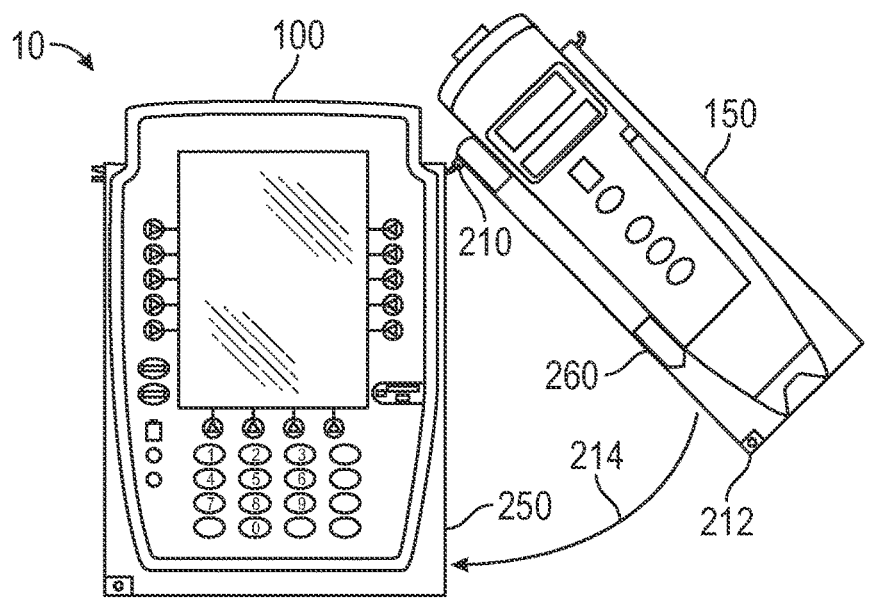
FIG. 3 illustrates a front view of a modular patient care system during an attachment process, in accordance with some embodiments.

FIG. 3 illustrates the modular patient care system 10 during an example of an attachment process or sequence that can be used to releasably attach a pair of modules to each other. FIG. 3 shows a front view of the system with the left side 260 of functional module 150 being attached to the right side 250 of the interface module 100. As seen in FIG. 3, an upper end portion of the functional module 150 can include a retention component 210 on its left side, which can mate with a complementary retention component on the upper end portion of the right side of the adjacent module. The retention component 210 can be mated by moving the left side 260 of the functional module 150 into the right side 250 of the interface module 100 at an angle, so that the retention component 210 of the functional module can mate, seat, or insert into the complementary retention component of the interface module 100. Upon mating or engagement of the retention components, the mated retention components or upper end portions of the adjacent modules can then provide an anchor or pivot point for the functional module 150 to be rotated thereabout. Upon rotation of the functional module 150 (e.g., in direction of arrow 214 about the retention component 210), the bottom end portion of the functional module 150 can be secured against the bottom end portion of the interface module 100, to engage a latch mechanism 212 at the bottom end portion of the functional module 150 with a complementary mechanism at the bottom end portion of the interface module 100. Upon latching engagement of the latch mechanism 212, the adjacent modules may be secured in a side by side arrangement (for example as seen in FIG. 1A). These steps may be performed by a user (e.g., a medical practitioner or technician) gripping and manipulating the functional module 150 to move the functional module and secure the adjacent modules together.

Figure 4:
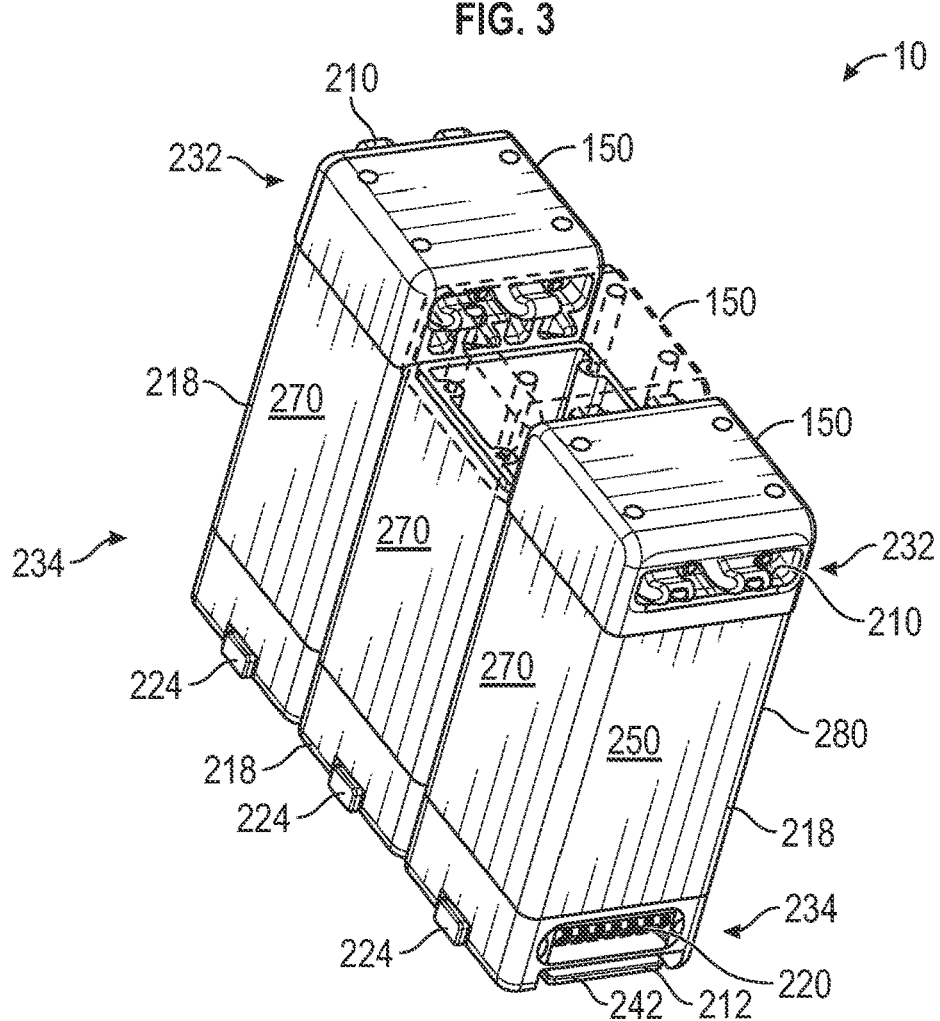
FIG. 4 illustrates a right perspective view of a modular patient care system, in accordance with some embodiments.
Figure 5:
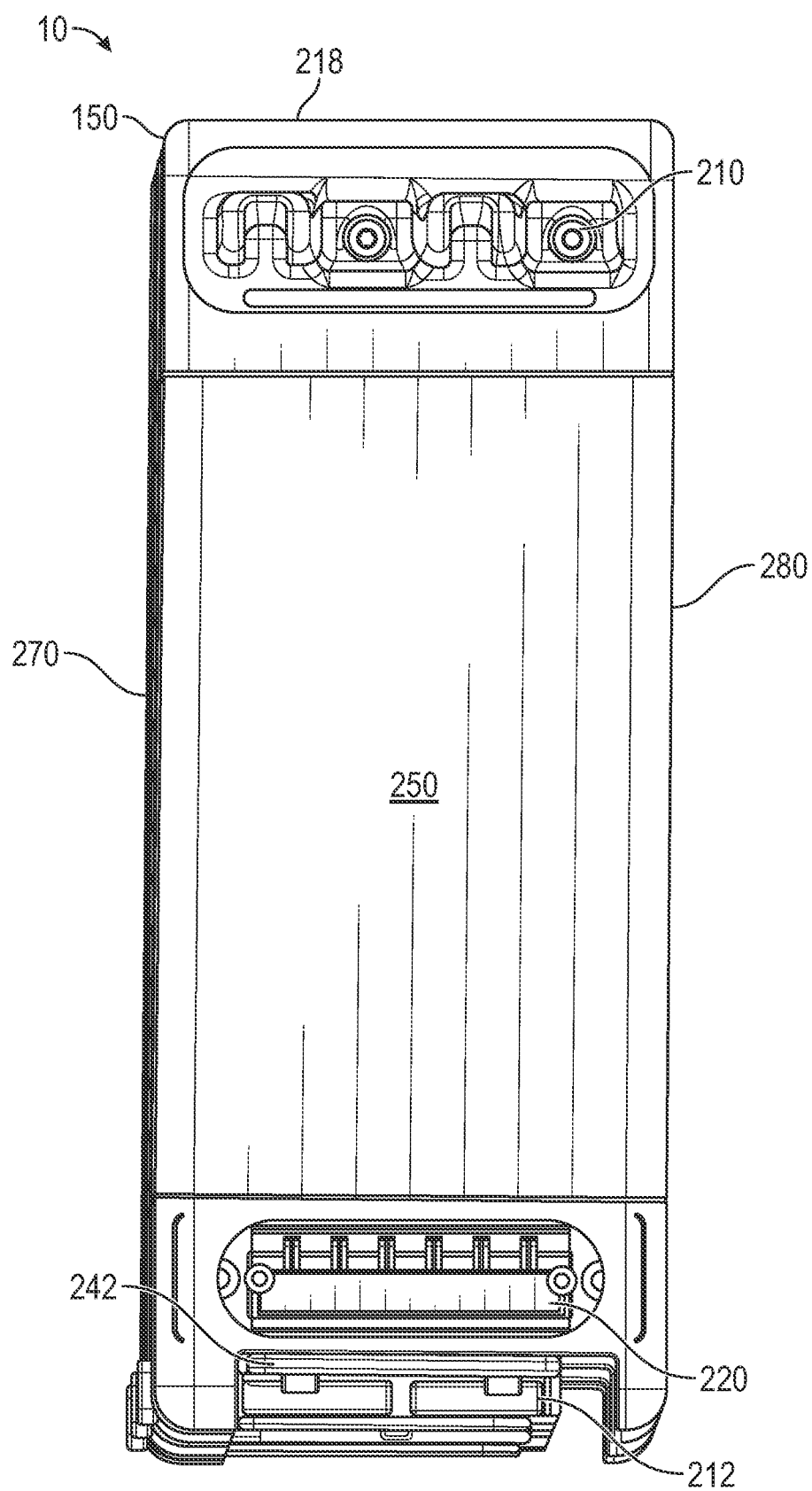
FIG. 5 illustrates a right side view of a modular patient care system, in accordance with some embodiments.
Figure 6:
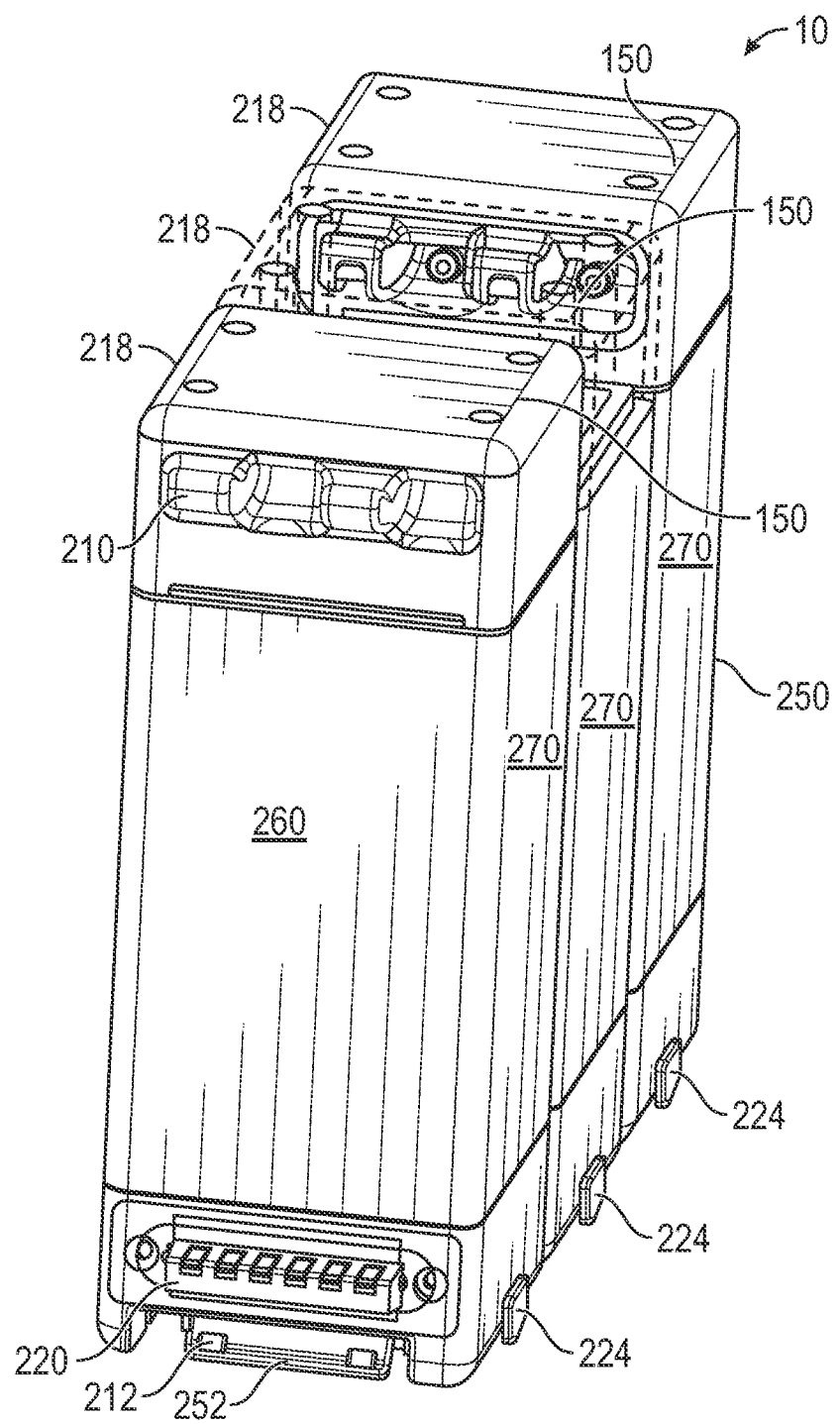
FIG. 6 illustrates a left perspective view of a modular patient care system, in accordance with some embodiments.
Figure 7:
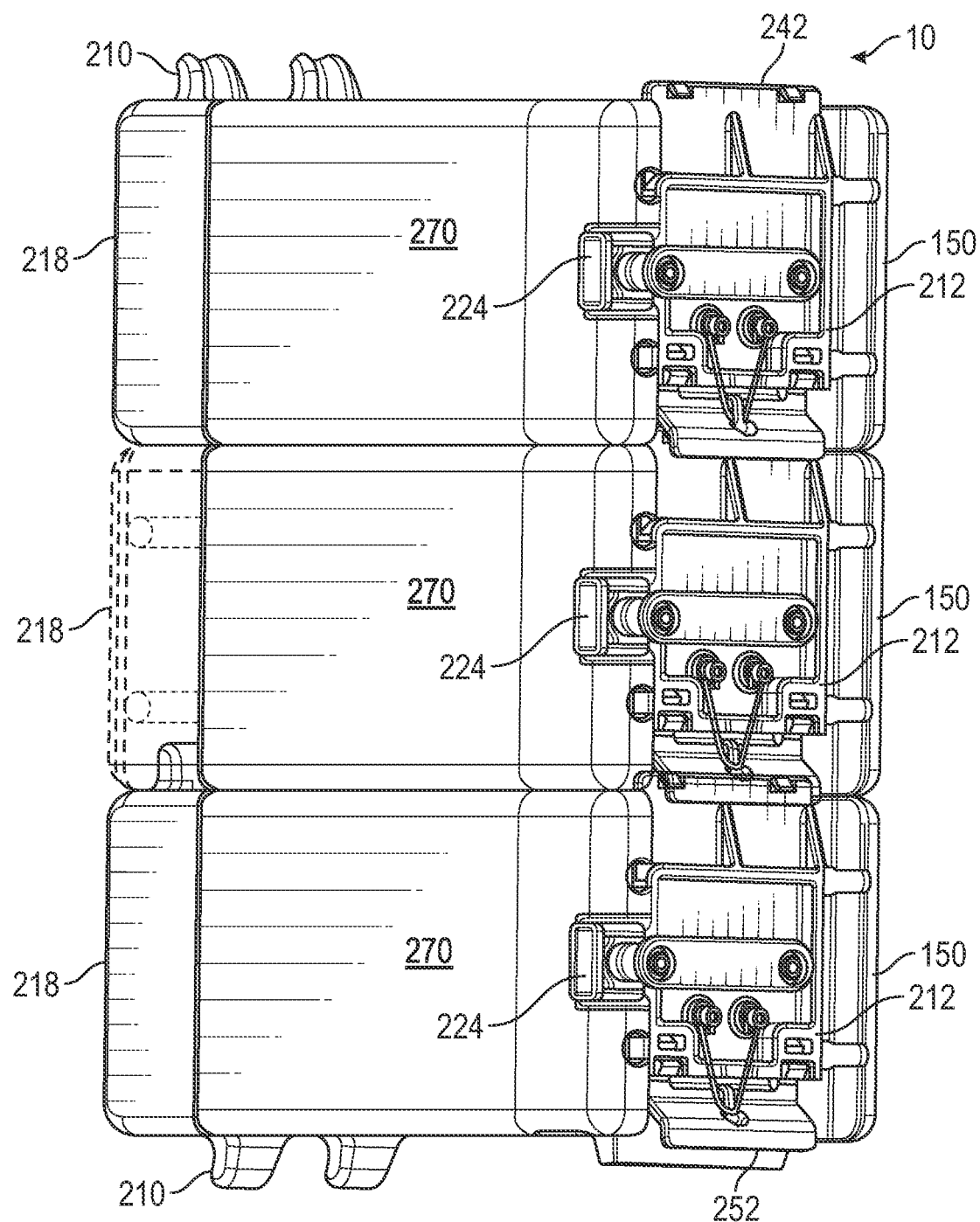
FIG. 7 illustrates a bottom perspective view of a modular patient care system, in accordance with some embodiments.

FIGS. 4-7 illustrate various views of a mechanical and electrical attachment mechanism for the modular patient care system 10, in accordance with some embodiments. FIG. 4 shows a right perspective view, FIG. 5 shows a right side view, FIG. 6 shows a left perspective view, and FIG. 7 shows a bottom side view, with each of these figures showing the modular patient care system 10 with multiple functional modules 150 attached together. FIGS. 8-12 illustrate enlarged views of various components of the attachment mechanism, in accordance with some embodiments.

As seen in the figures, each of the functional modules 150 can include a housing or casing 218, which can house internal components of the module therein, such as, for example, one or more processors, memory, batteries, power supplies, circuitry, pumps, and/or motors. Attachment mechanisms are disposed on opposing sides or opposing side surfaces of each housing 218 to permit the housings to be attached together in a side-by-side arrangement. Mechanical and electrical attachment mechanisms, including mechanical retention members 210, electrical connectors 220, and latch mechanisms 212 are located at the opposing attachment sides of each housing 218 and are configured to mate with each other to secure the attachment sides of adjacent modules together. The mechanisms shown can be configured to facilitate an attachment sequence like that shown and described above with respect to FIG. 3. An actuator 224 is coupled to the latch mechanism 212 of each module 150 and can operate the latch mechanism 212 to release or detach the module from the adjacent module attached to its right side 250 and/or its left side 260. Although the mechanisms are described with respect to functional modules 150, it is contemplated that the mechanism can be applied to any other suitable modules of a modular system, including, for example, the interface module 100.

Referring to FIGS. 4-7, each housing 218 is shown as having a generally rectangular box shape with a front side 270, a rear side 280, a right side 250, and a left side 260. The front side 270 corresponds to the front side of the module 150 (e.g., as seen in FIG. 1A), and the rear side 280 is opposite to the front side and corresponds to the rear side of the module. The left side 260 and the right side 250 each adjoin the front side 270 and the rear side 280, with the left side 260 corresponding to the left side of the module when viewed facing the front side 270, and the right side 250 being opposite to the left side 260 and corresponding to the right side of the module when viewed facing the front side 270. The left and right sides correspond to attachment sides of the modules that are each configured to mate with the complementary attachment sides of adjacent modules.

On each of the attachment sides, i.e., the left side 260 and the right side 250 in this example, a retention component 210 is located at an upper end portion 232 of the housing 218, and a latch mechanism 212 is located at a lower end portion 234 of the housing 218. An electrical connector 220 is shown as a separate connector from the latch mechanism 212 and retention component 210, located intermediate the latch mechanism 212 and retention component 210, and located closer to the latch mechanism 212 than the retention member 210. The actuator 224 is implemented as a mechanical actuation button coupled to the latch mechanism 212 and located at the bottom end portion 234 on the front side 270 of the housing 218.

Figure 8:
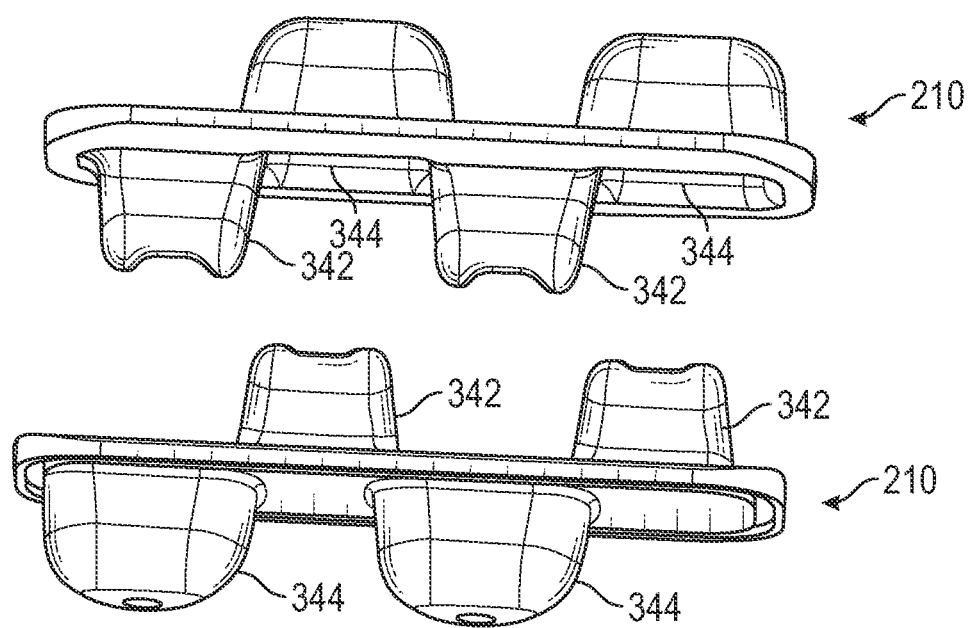
FIG. 8 illustrates an enlarged view of a pair of retention components for a modular patient care system, in accordance with some embodiments.
Figure 9:
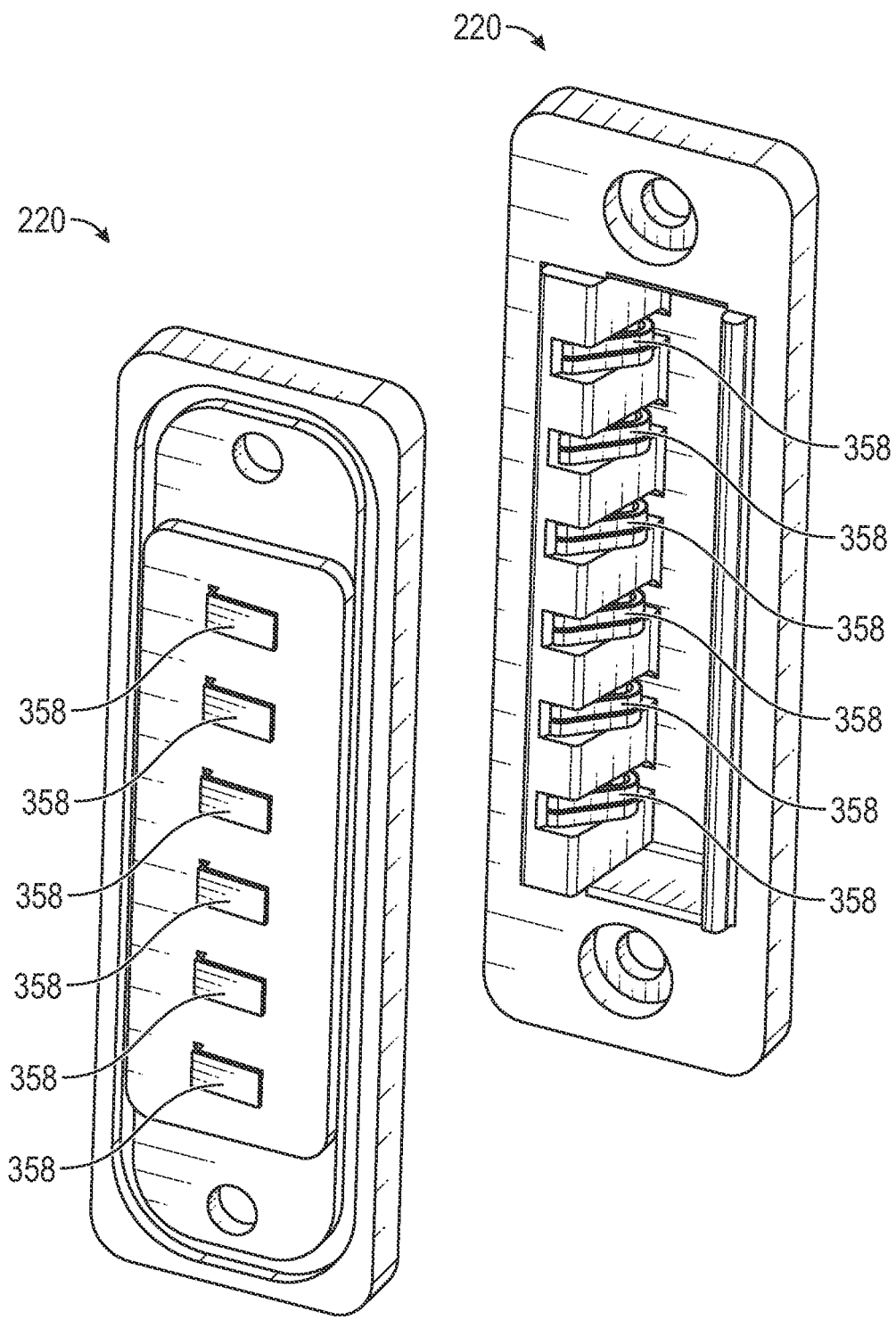
FIG. 9 illustrates an enlarged view of a pair of electrical connectors for a modular patient care system, in accordance with some embodiments.

The retention components 210 are configured to mate with each other to provide structural support for end portions of adjacent modules, without necessarily being configured to lock them together. As further seen in the enlarged view of FIG. 8, the retention components 210 include features that permit them to slidingly engage each other to facilitate retaining support of the corresponding ends of the modules. Each retention component 210 can include one or more protrusions 342, and one or more recesses 344 that are each configured to receive a protrusion from an adjacent retention component slidably inserted therein. In FIG. 8, the protrusions 342 and recesses 344 have rounded profiles, which may enhance the ease with which protrusions 342 can be slid into the recesses 344. Also, multiple protrusions 342 and multiple recesses 344 (in this case a pair of each), are shown disposed across the width of the retention component 210, with the recesses interposed between the protrusions and vice versa, which may enhance the balance of support provided by the retention component across the width of the attachment side compared to an implementation utilizing only one protrusion and recess on each retention component. The retention components 210 can be made from or can otherwise include electrically conductive materials (e.g., metal) so that the retention components can provide a grounding path between attached modules.

The electrical connectors 220 are configured to make electrical connections between adjacent modules upon mechanical attachment. As further seen in the enlarged view of FIG. 9, the electrical connectors 220 can each include multiple contacts 358 that provide multiple respective channels for exchanging signals between the modules. Each channel may correspond to a particular signal, such as a ground connection, a data connection, or a power connection. The contacts 358 of adjacent connectors 220 are configured to make galvanic contact with each other, upon mechanically engaging or attaching adjacent modules together, to permit the exchange of signals there between.

Figure 10:
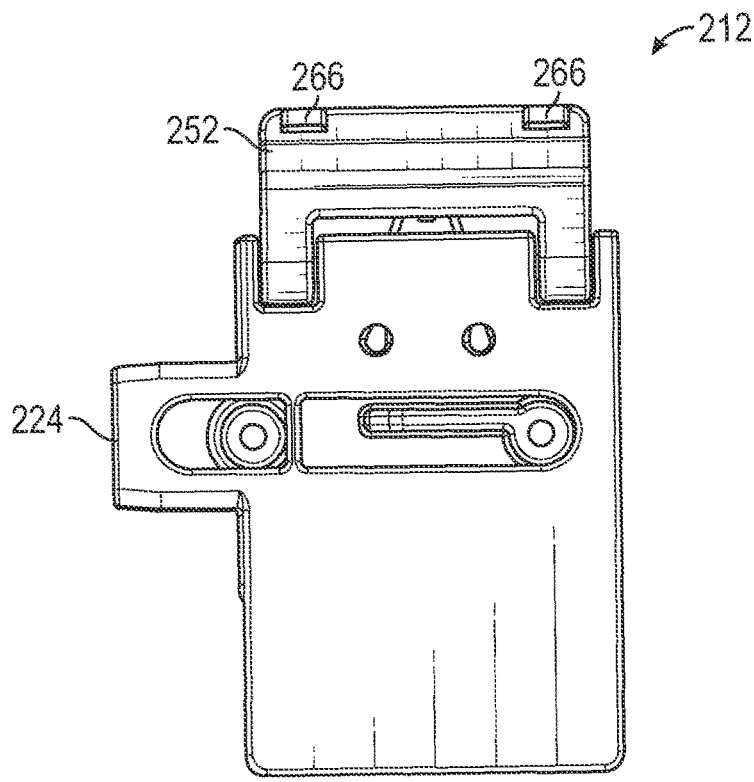
FIG. 10 illustrates an enlarged top view of a latch mechanism for a modular patient care system, in accordance with some embodiments.
Figure 11:
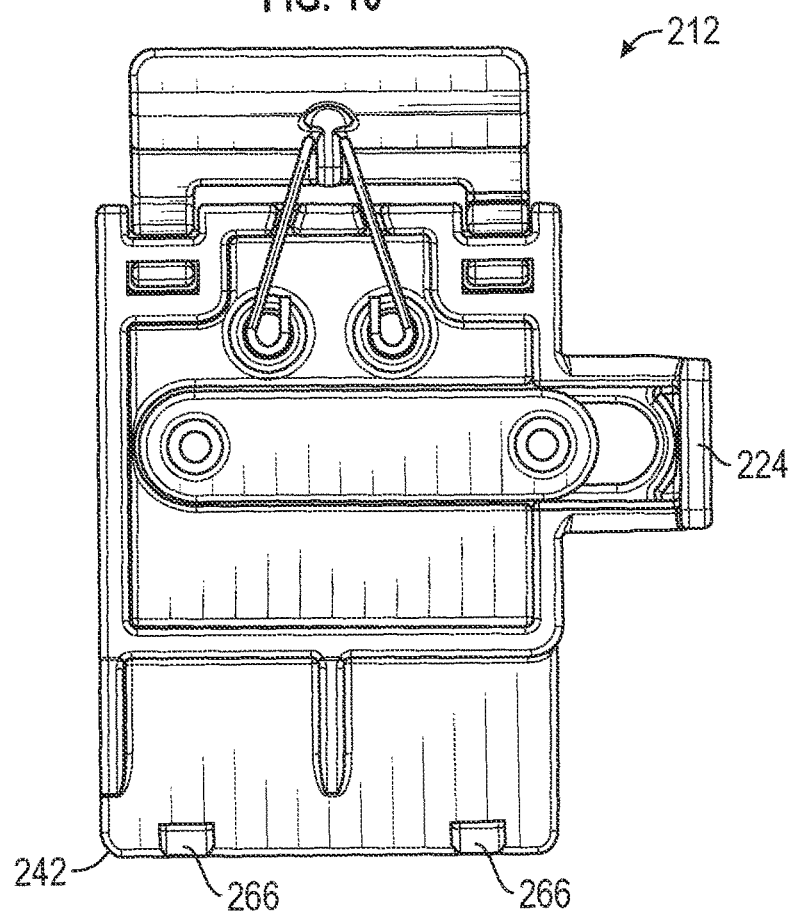
FIG. 11 illustrates an enlarged bottom view of a latch mechanism for a modular patient care system, in accordance with some embodiments.
Figure 12:
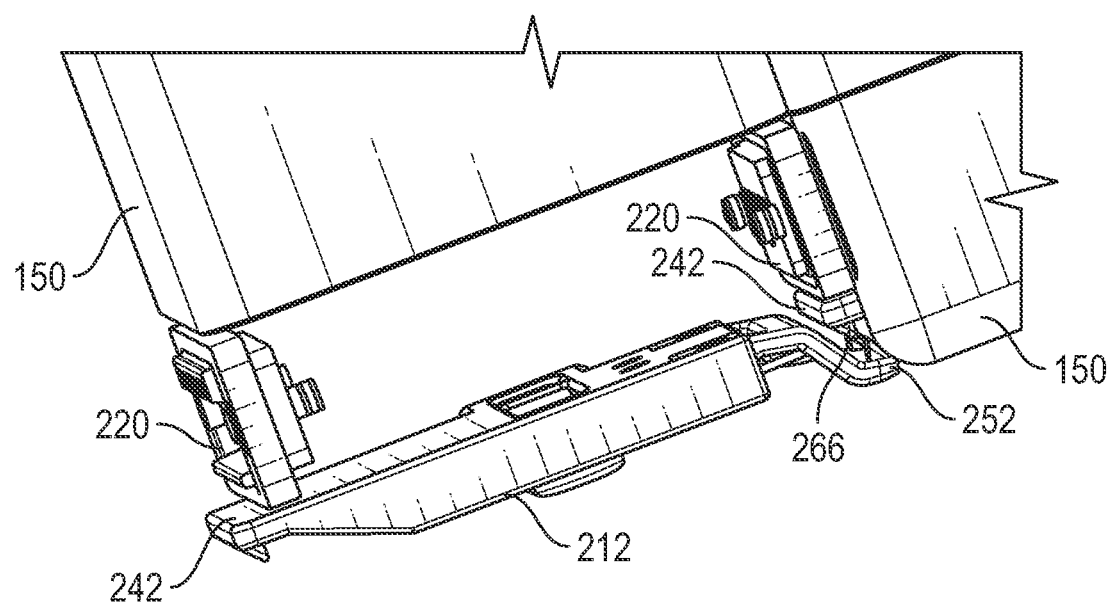
FIG. 12 illustrates an enlarged view of a latch mechanism engaged with an adjacent module, in accordance with some embodiments.

The latch mechanisms 212 are configured to mechanically secure adjacent modules together via latching engagement between the adjacent modules. FIGS. 10-11 show enlarged views of the latch mechanism 212 of the example of FIGS. 4-7, in which FIG. 10 is a top side view and FIG. 11 is a bottom side view. FIG. 12 shows an enlarged view of the latch mechanism 212 in an engaged configuration in which it is latched onto an adjacent module.

As further seen in the enlarged views of FIGS. 10-12, each latch mechanism 212 can include a catch member 242, and a movable engagement member 252 that is configured to engage with and latch onto the catch member 242 of an adjacent module. Each of the engagement member 252 and the catch member 242 can include complementary hook features 266 that engage with each other for securely retaining the latch in an engaged configuration. The actuator 224 can include an actuation button that is fixed to components of the latch mechanism and configured to move or translate components of the latch mechanism. The movement of the latch mechanism 212 based on operation of the actuation button can release the hook features 266 to disengage the engagement member 252 from the catch member 242. In the example shown in FIGS. 4-7, the catch member 242 is located at the right side 250 of each module, while the engagement member 252 is located at the left side 260 of each module and is configured to engage the catch member 242 of the adjacent module to the left. It is contemplated that other arrangements are possible, including, for example, the reverse in which the catch member 242 is located on the left side and the engagement member is located on the right side. Also, while the catch member 242 is shown as part of a latch component that is attached to the housing 218, it is contemplated that the catch member 242 may be implemented as a fixed part of the housing 218, e.g., with hook features 266 formed as an integral part of the housing 218.

Although a particular arrangement of the attachment components on the left and right sides of the housings are shown, it is contemplated that various other arrangements, configurations, and positions are possible for these attachments components. For example, the locations of the latch mechanism 212 and retention component 210 can be reversed with respect to the upper and lower end portions, so that the retention component 210 is located at the bottom end portion 234 and the latch mechanism 212 is located at the upper end portion 232. As another example, these components can be located on other opposing or non-opposing sides of the housing 218 for other types of attachment or coupling configurations for the set of modules.

Figure 13:
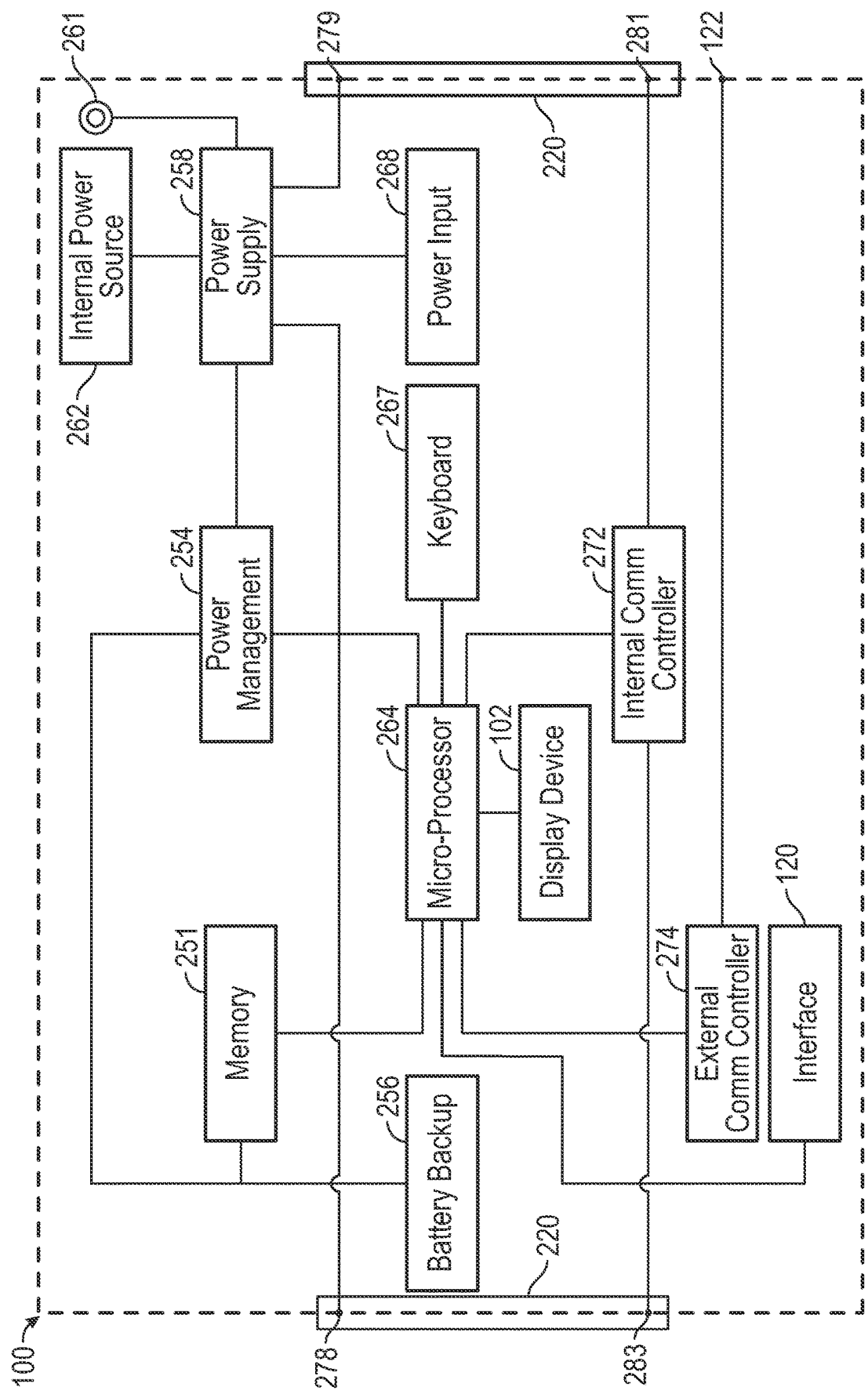
FIG. 13 is a schematic diagram of an example of an interface module, in accordance with some embodiments.

FIG. 13 is a schematic diagram of an example of the interface module 100, in accordance with some embodiments. In the example shown in FIG. 13, interface module 100 contains a power input 268 for receiving power from an external power source and forwarding that power to power supply 258. Interface module 100 also contains an internal power source 262, which may be used to maintain power to the system functions, including memory, when interface module 100 is disconnected from an external power source. Power supply 258 can convert power from either external power input 268 or internal power source 262 to voltages that are appropriate for operating parts of the system. Power management unit 254 can control the switchover between the two power sources, control the charging of internal power source 262, monitor the remaining capacity of internal power source 262, monitor system power consumption under battery operation, and use system power consumption and remaining battery capacity to estimate remaining system runtime on internal power source 262. Power supply 258 can also supply power to the rest of the system through power ports 278 and 279 as well as to audio alarm 261, thereby providing audio functionality of the system.

Microprocessor 264 and memory 251 can receive and process data and commands from the user, as well as communicate with and control functional modules 150 and other devices external to the system. It is to be understood that memory 251, as well as other memories in the patient care system, may be any type of memory or any combination of memories that can be erased and reprogrammed. Examples of such memories include, but are not limited to, battery-backed random access memory (RAM) and flash electronically erasable programmable read only memory (FLASH EEPROM). Battery backup 256 can provide power to memory 251 to maintain the information stored in the memory in the event of loss of power from both the power input 268 and the internal power source 262. Interface module 100 also contains a keyboard 267 (which includes hard keys 104 and soft keys 106) and a display device 102, as discussed in conjunction with FIGS. 1A-2 above.

Power ports 278 and 279, fed by power supply 258 can provide power to functional modules 150 through connectors 220. Connectors 220 can also contain internal communication ports 283 and 281, respectively, which provide a data and command interface with attached functional units 150. Ports 283 and 281 can be controlled by internal communications controller 272, which in turn can be controlled by microprocessor 264. Finally, external communications controller 274 can control the command and data flow through interface ports 122, while microprocessor 264 can directly control communication interface 120.

Figure 14:
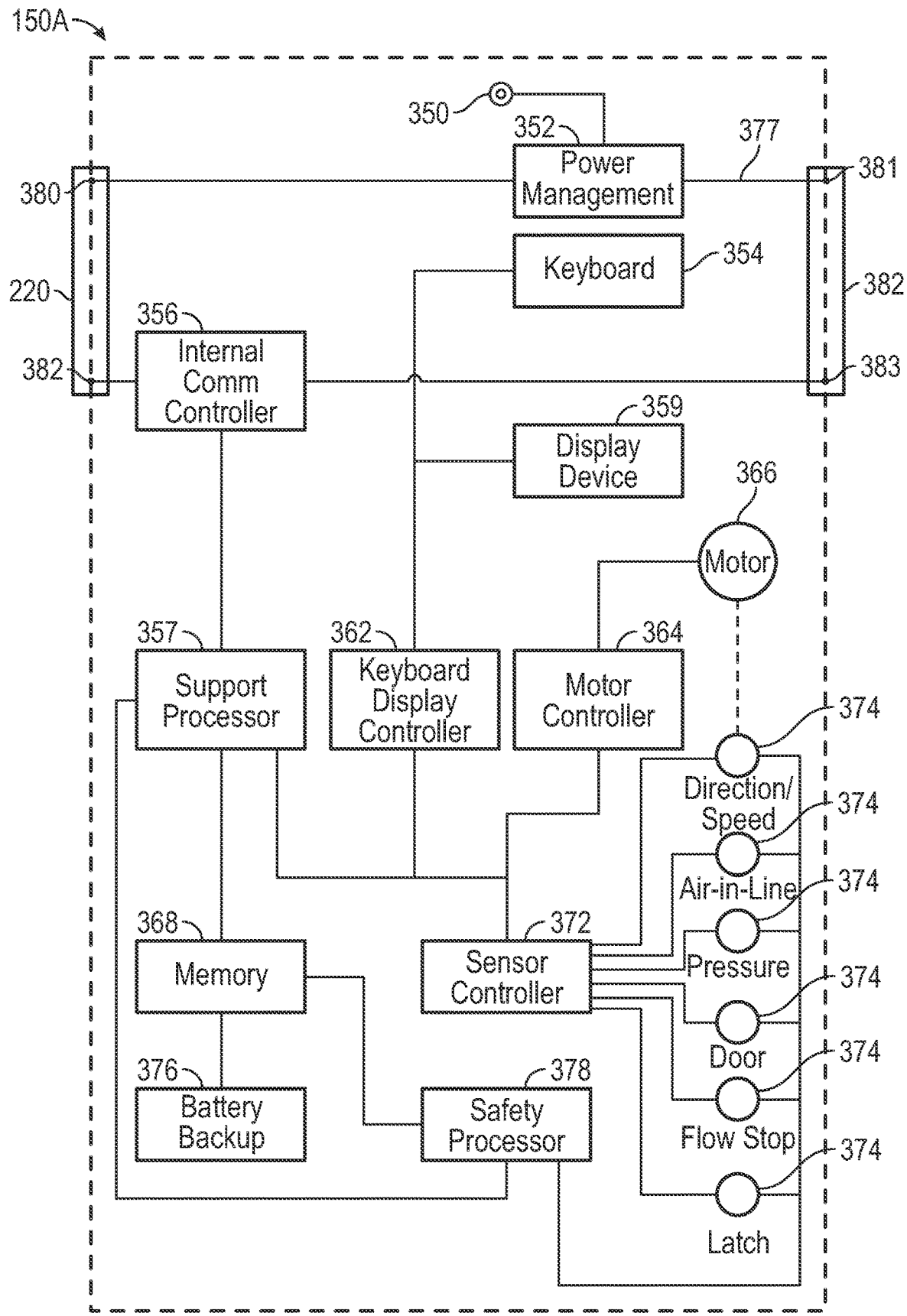
FIG. 14 is a schematic diagram of an example of a functional module, in accordance with some embodiments.

FIG. 14 is a schematic diagram of an example of a functional module, in accordance with some embodiments. In this example, the functional module is configured as infusion pumping module 150A. FIG. 14 illustrates the various aspects of a control system for infusion pump module 150A. Display device 359 can include rate display 154, channel display 152, and the various visual indicators 164 discussed in conjunction with FIG. 2. Keyboard 354 can be made up of the various buttons including hard keys as also previously discussed, and can be controlled, along with display device 359, by keyboard/display controller 362. Support processor 360 and associated memory 368 can be configured to receive and process data and commands from the user, as well as communicate with the attached interface module. For example, support processor 360 and memory 368 can be configured to perform calculations for a designated infusion using infusion data entered by the user. Memory 368 can have a battery backup 376 so as to maintain the information stored in memory when the functional module is not receiving power from an external source. Battery backup 376 may also be used to power audio alarm 350, which may emit a signal when an infusion is complete or there is a failure of the main power source. Power management unit 352 can obtain power from power ports 380 or 381, which are included in the electrical connectors 220 which connect the functional modules to the interface modules or other functional modules. Electrical connectors 220 can connect through power line 377 and distribute the power to the components of infusion pump module 150A. Like the interface module 100, infusion pump module 150A can also contain an internal communications controller 357, which may be configured to send or accept data or commands from the interface module through communication line 379 and communication ports 382 and 383, which can also be contained in the electrical connectors 220. These power and communication ports connected by the power and communication lines can allow functional units to be connected side-by-side, yet still communicate with the interface module through intervening functional modules while not directly attached to the interface module.

Infusion pump unit 150A can also include components to facilitate pumping, such as motor controller 364 for controlling pump motor 366 and sensor controller 372 to obtain indications from sensors 374. Sensors 374 may be used to detect pump mechanism speed and fluid pressure, air-in-line, and flow stoppage. Motor controller 364 and pump motor 366 may, for example, include any suitable peristaltic pump motor/motor controller combination. Pump motor 366 can be configured to urge fluid from a fluid reservoir through an infusion set to a vascular access device (e.g., a catheter) by peristaltic motion. It is contemplated that a variety of commercially available fluid reservoirs, sets, vascular access devices and other infusion materials can be used in conjunction with infusion pump module 150A.

Sensor controller 372 can be configured to receive signals from sensors 374, which for example sense pump motor direction and speed, the presence of air in the fluid path, fluid path pressure, open or closed state of the pump door, open or closed state of a flow stop device, and/or movement of a latch mechanism, and forward this information to support processor 360. If support processor 360 determines that an undesired or other predetermined event is occurring, the support processor is capable of taking further action such as placing pump unit 150A in an advisory or alarm state, stopping the infusion, shutting down the pump unit, and/or forwarding information to the attached interface module for full system shutdown.

Safety processor 378 can be configured to monitor these same signals from sensors 374. Safety processor 378 can also receive pump operating parameters from support processor 360, such as current infusion rate, VTBI, and fluid path pressure alarm limits. Safety processor 378 can be configured to independently calculate values, such as the appropriate motor speed from these parameters, and using these values, monitors sensor 374 for proper pump motor direction and speed, the presence of air in the fluid path, fluid path pressure, open or closed state of the pump door, and open or closed state of the flow stop device. When safety processor 378 determines that an undesired event is occurring, this information can be forwarded to support processor 360 for further action, or the safety processor may independently shut down the functional module.

Infusion pump module 150A (or any other functional module 150) can be configured without a local source of power (with the exception of the memory retention and the audio alarm features described above), and therefore may not be able to continue to operate in the event of failure of the main power source, such as when the functional module is detached from the interface module. This can ensure that the functional unit is not operated without the safety and control features provided by the interface units. Also, the simplified commands available directly at the pump functional unit are not intended to replace the interface capabilities of advanced interface unit 100 or basic interface unit 200. However, when provided with power and the necessary input values (such as VTBI and infusion duration) from the interface unit, the infusion pump unit as a functional unit is capable of controlling all aspects of an infusion.

Interface module 100 can also include a sensor 374, which is configured to detect mechanical movement of latch mechanism 212. The latch sensor can be configured to detect movement of the latch mechanism that is indicative of engagement and/or disengagement of the latch mechanism 212 with an adjacent module. The latch sensor can be used alone or in combination with electrical information detected through the electrical connector 220 to determine when the interface module is attached or detached from an adjacent module. Such signal can be used by a processor of the system, such as support processor 356, to enforce a requirement that the latch mechanism be engaged before permitting core functionalities of the modules to operate, such as pumping operations, diagnostic measurement operations, or the like. For example, the system can be configured to prevent such operations until detecting movement of the latch mechanism that is indicative of engagement and secure attachment between modules, then upon detecting the latch movement the system may enable such operations in response.

Figure 15A:
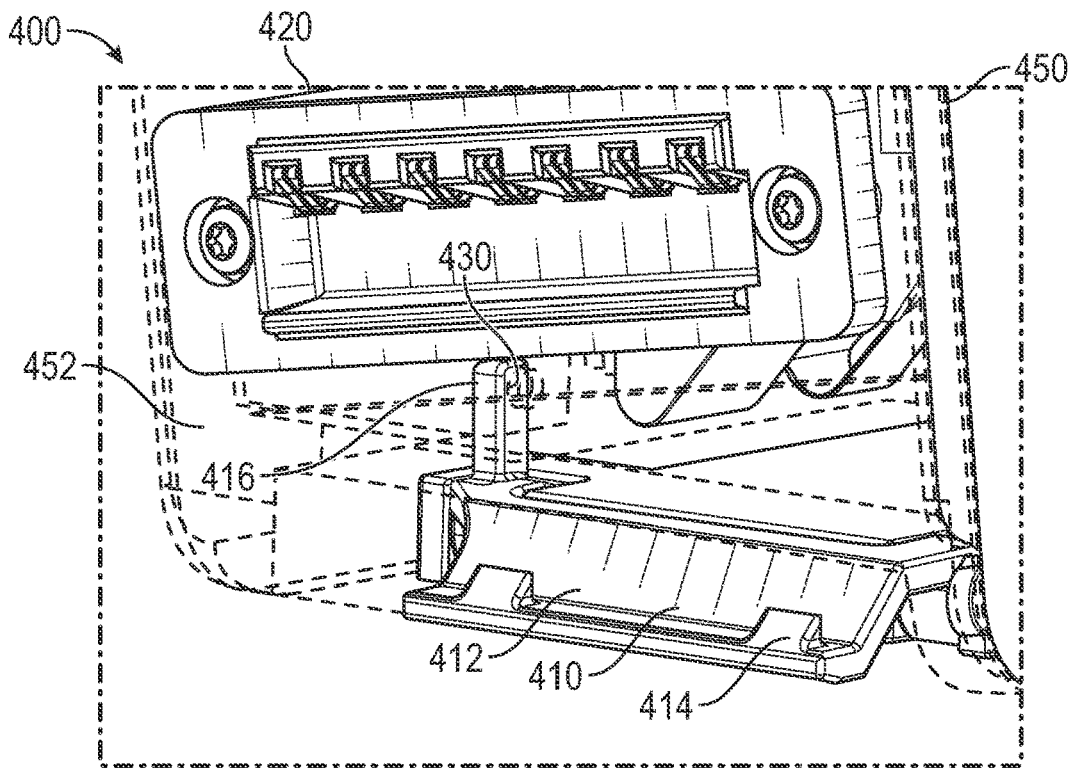
FIGS. 15A-15C illustrate perspective views of a latch mechanism for a module of a patient care system, in accordance with some embodiments.
Figure 15B:
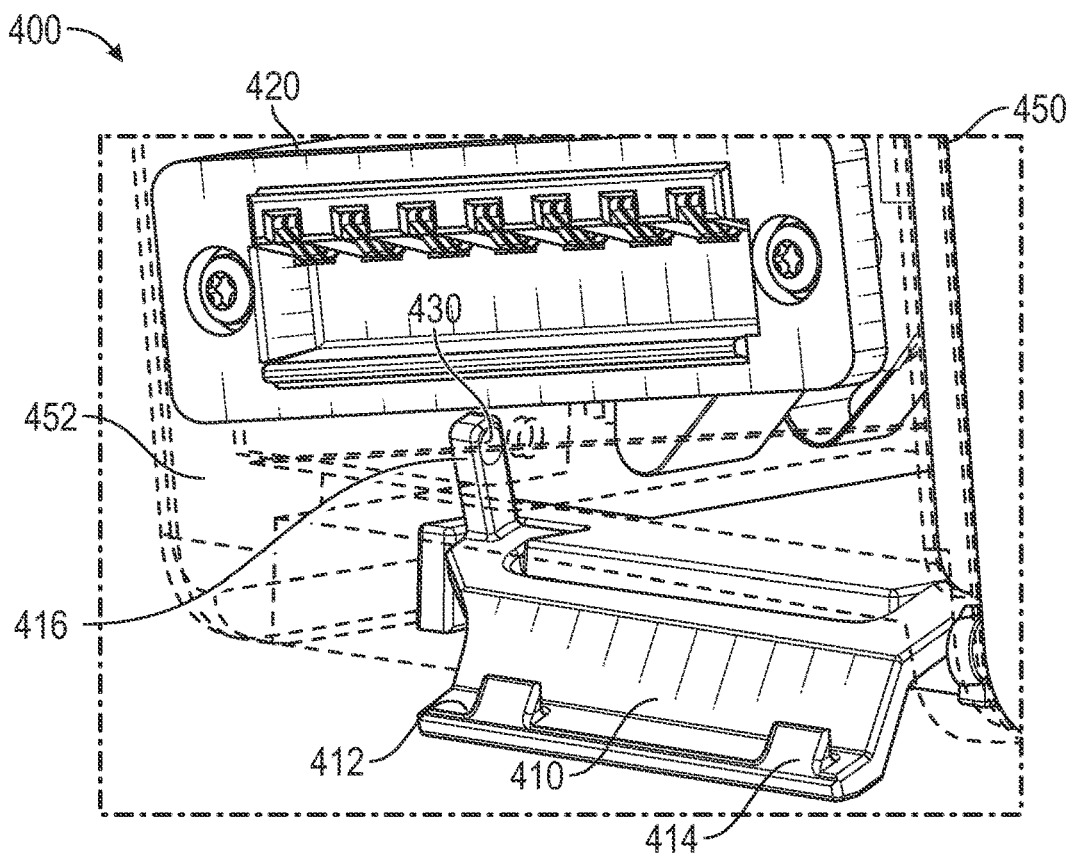
Figure 15C:
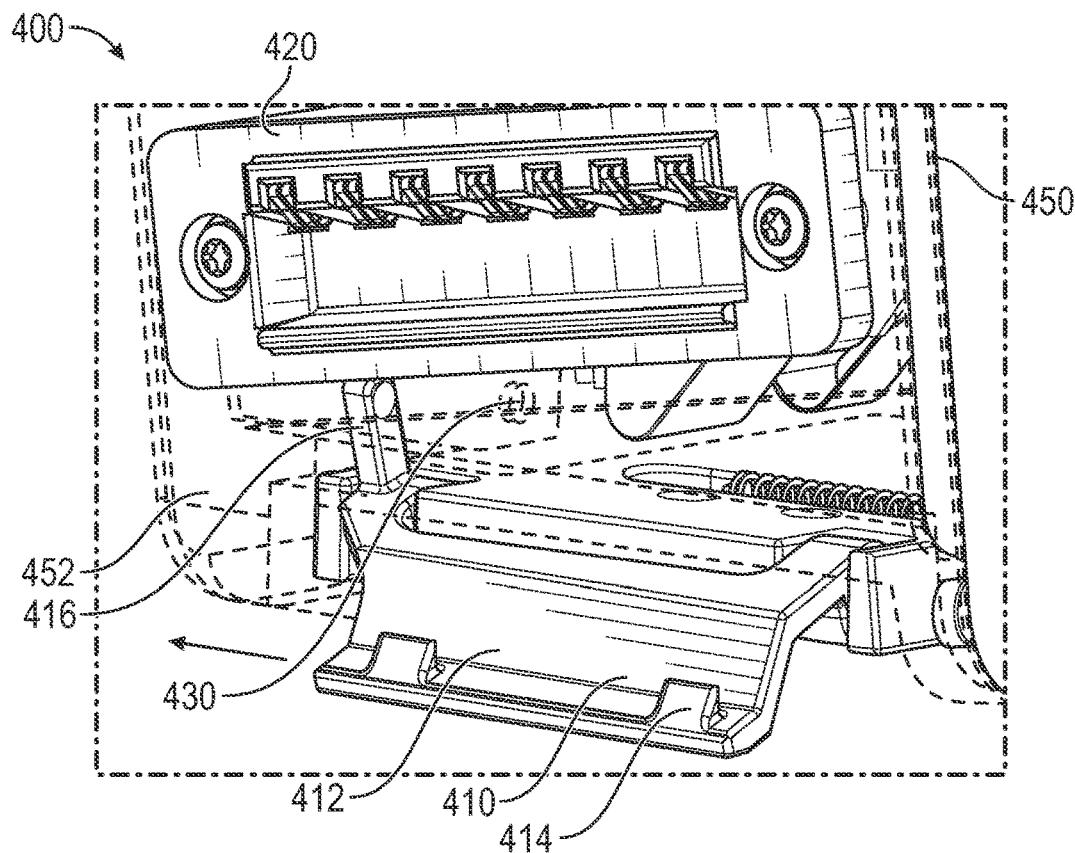

FIGS. 15A-15C illustrate perspective views of a latch mechanism 410 for a module patient care system 400, in accordance with some embodiments. In the depicted example, the latch mechanism 410 allows for a mechanical connection between functional modules 450. By engaging the latch mechanism 410, a functional module 450 can be mechanically coupled to another functional module 450 or another component of a patient care system 400.

Along with allowing for mechanical coupling and decoupling of functional modules 450, the latch mechanism 410 can allow for electrical connectors 420 to be properly engaged and released as desired. Therefore, by engaging the latch mechanism 410, a functional module 450 can be mechanically and electrical coupled to another component of the patient care system 400.

With reference to FIG. 15B, during operation, the latch mechanism 410 can be rotated relative to the module body 452 to move the latch body 412 between an unlatched position and a latched position. In the depicted example, the latch body 412 can be in an unlatched position to allow the functional module 450 to be disengaged or released from another component of the patient care system 400. As can be appreciated, the electrical connector 420 of the functional module 450 can also be electrically disconnected in the unlatched position.

During operation, the latch mechanism 410 can be rotated relative to the module body 452 to move the latch body 412 into a latched position. In the depicted example, the latch body 412 can be moved clockwise or upward toward the module body 452 to move the latching mechanism into the latched position. In some embodiments, the latch body 412 can include hook protrusions 414 extending from the latch body 412 to allow the latch body 412 to positively engage with a complimentary functional module 450 or other component of the patient care system 400. In some embodiments, the hook protrusions 414 can engage in a complimentary recess or groove of a mating component. Optionally, the hook protrusions 414 can have a resilient construction.

With reference to FIG. 15C, during operation, the latch mechanism 410 can be translated relative to the module body 452 to move the latch body 412 between an unlocked and locked position. In the depicted example, the latch body 412 can be in an unlocked position to allow the latch body 412 to rotate as described above. In some embodiments, the latch body 412 is moved inward relative to the module body 452 to an unlocked position. In some embodiments, an eject mechanism on the module body 452 is depressed to move the latch body 412 to the unlocked position.

In some embodiments, upon release of the eject mechanism, the latch body 412 can translate into a locked position. Optionally, the latch body 412 can be spring loaded or biased to the locked position. In the locked position, the latch body 412 may prevent the rotation of the latch mechanism 410, preventing inadvertent engagement or disengagement of the functional module 450 within the patient care system 400.

In some embodiments, the latch mechanism 410 can include a latch sensor 430 to detect movement of the latch body 412 relative to the module body 452. In the depicted example, the latch sensor 430 can be disposed on or within a latch extension 416 disposed within the module body 452. During operation, the latch sensor 430 can move with the latch body 410 as the latch body 412 is rotated and/or translated as described above. In some embodiments, the latch sensor 430 can be fixed within the module body 452 and sense the movement of the latch body 412.

In some embodiments, the latch sensor 430 can be a hall effect sensor, an optical interrupt sensor, a capacitance sensor, and/or an inductance sensor. Optionally, the latch sensor 430 can withstand or resist fluid ingress. In some embodiments, the latch sensor 430 can be unidirectional and can detect the rotation or translation of the latch body 412. In some embodiments, the latch sensor 430 is omnidirectional and can detect the rotation and the translation of the latch body 412. Optionally, the latch body 412 can include a magnet that is adhered, affixed, or overmolded therein to permit the latch sensor 430 to detect rotation and/or translation of the latch body 412.

In the depicted example, the latch sensor 430 can detect the translation of the latch body 412, such as when an eject mechanism translates the latch body 412. By detecting the motion of the latch mechanism 410, the latch sensor 430 can be used to determine a user's intent, such as when a user intends to connect or disconnect a functional module 450.

Upon detecting that an unlatching event is occurring, the functional module 450 can log the event and switch power off to the electrical connector 420 to prevent arcing and corrosion. By sensing the position of the latch body 412, the functional module 450 can ensure that electrical signals are not sent to the electrical connector 420 when the functional module 450 is unlatched.

Similarly, the latch sensor 430 can be used to detect the rotation of the latch body 412, such as when the latching mechanism 410 is engaged with a receiving functional module 450. By detecting the rotational motion of the latch mechanism 410, the latch sensor 430 determine if the latch body 412 is being engaged or disengaged with a complimentary functional module.

Therefore, during operation, the latch sensor 430 can be used to determine when electrical connections to the electrical connector 420 are made and mechanical connections at the latch mechanism 410 are securely made between adjacent modules. Upon this determination, electrical power can be switched on in a controlled fashion, and intra-module communication can be initiated.

Figure 16:
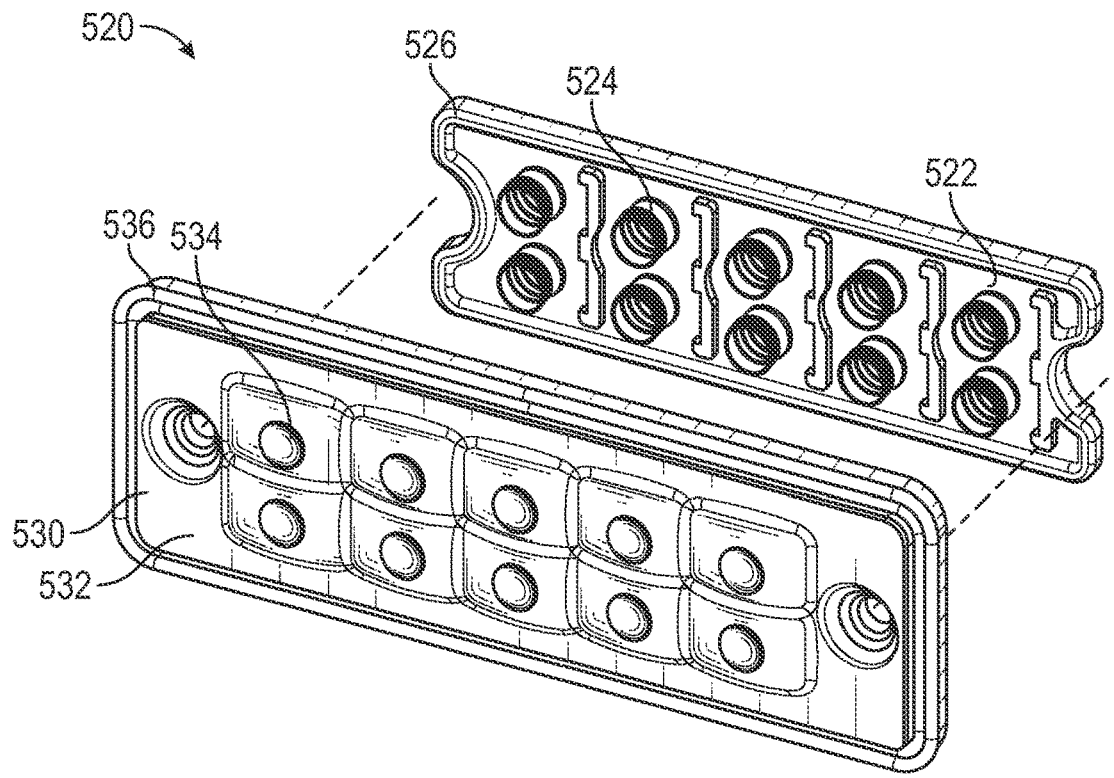
FIG. 16 is an exploded perspective view of an electrical connector for a module of a patient care system, in accordance with some embodiments.

FIG. 16 is an exploded perspective view of an electrical connector 520 for a module of a patient care system, in accordance with some embodiments. In the depicted example, the radial seal 530 can protect the electrical connector 520 from liquids such as cleaning chemicals that may damage the structure of the electrical connector 520 or may affect the electrical connection provided by the electrical connector 520.

In some embodiments, the radial seal 530 is an elastomeric seal that covers the electrical connector 520 to protect the electrical connector 520 from liquids such as cleaning chemicals. The radial seal 530 can be formed from any elastomeric material or any other resilient material. In some embodiments, the radial seal 530 can be a urethane casting or overmold. The radial seal 530 can include a seal body 532 to generally cover the connector face 522 of the electrical connector. Optionally, the radial seal 530 can extend over the connector edge 526. As illustrated, the seal edge 536 of the seal body 532 can extend over and engage with the connector edge 526. Optionally, the seal edge 536 and/or the connector edge 526 can allow for alignment of a mating connector with the electrical connector 520. In some embodiments, the seal 530 can be an axial seal.

As can be appreciated, the radial seal 530 can include apertures 534 to facilitate mechanical and electrical connection with the connector pins 524 extending from the connector face 522. Optionally, the various connector pins 524 can have different or staggered heights. By staggering the heights of the connector pins 524, the order of connection of the connector pins 524 can be controlled. For example, the longest pin 524 can come into contact with a mating connector before a shorter connector pin 524. Similarly, during disconnection, a shorter connector pin 524 can be disconnected before a longer connector pin 524 is disconnected. By altering the heights of the connector pins 524, certain functions or connections can be made active upon connection or remain active until the end of disconnection.

In some embodiments, the connector pins 524 can be cantilevered to be urged or biased toward a return or resting position.

Figure 17:
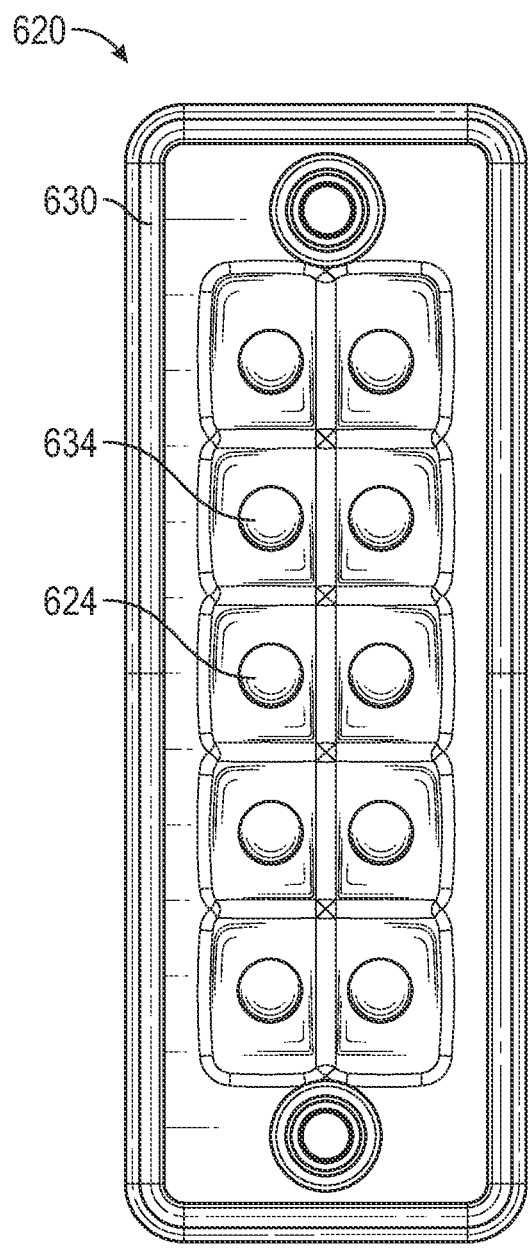
FIG. 17 is a top view of an electrical connector for a module of a patient care system, in accordance with some embodiments.

FIG. 17 is a top view of an electrical connector 620 for a module of a patient care system, in accordance with some embodiments. Similar to the electrical connector 520, the radial seal 630 can protect the electrical connector 620 from liquids such as cleaning chemicals that may damage the structure of the electrical connector 620 or may affect the electrical connection provided by the electrical connector 620.

In some embodiments, the radial seal 630 is an elastomeric seal that covers the electrical connector 620 to protect the electrical connector 620 from liquids such as cleaning chemicals. The radial seal 630 can be formed from any elastomeric material, such as a thermoplastic elastomer, or any other resilient material. In some instances, the radial seal 630 can extend over the outside diameter of the electrical connector 620. In some embodiments, the radial seal 630 can be bonded or otherwise mechanically interlocked to the substrate of the electrical connector 620. As can be appreciated, the radial seal 630 can hold portions of the electrical connector 620 in place. Advantageously, the radial seal 630 can prevent peeling or separation of the electrical connector 620.

As can be appreciated, the radial seal 630 can include apertures 634 to facilitate mechanical and electrical connection with the connector pins 624 extending from the electrical connector 620. In some embodiments, the apertures 634 can be undersized to prevent molding flash from covering the connector pins 624.

Figure 18:
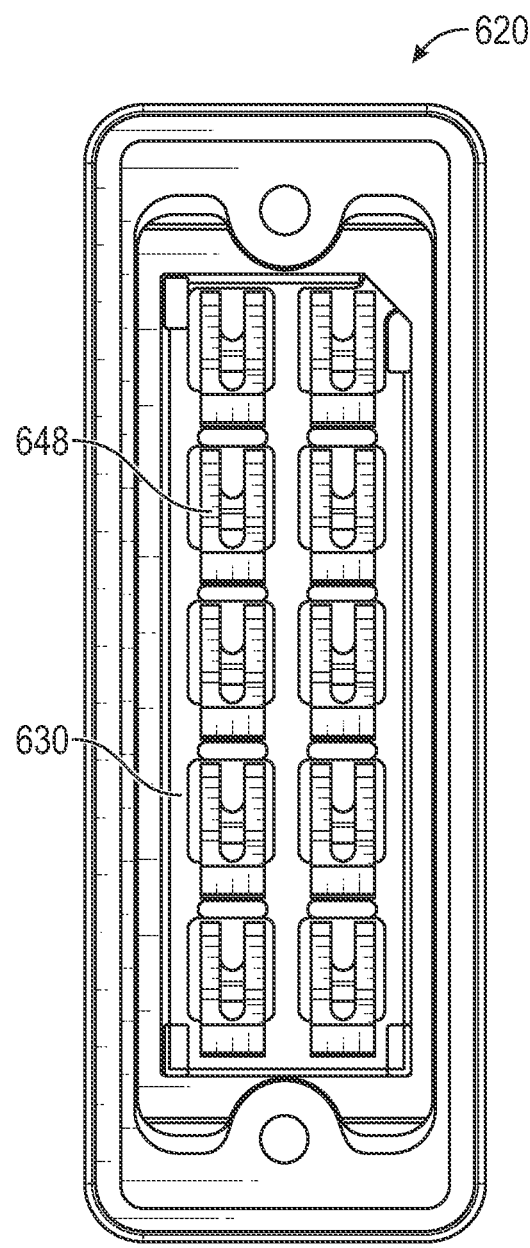
FIG. 18 is a bottom view of the electrical connector of FIG. 17.
Figure 19:
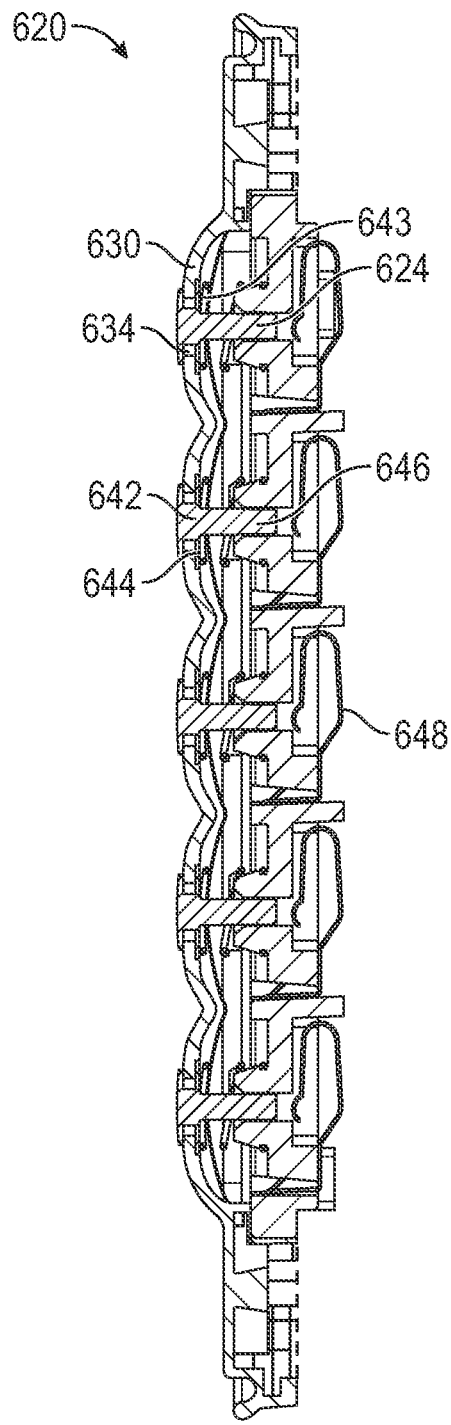
FIG. 19 is a cross-sectional view of the electrical connector of FIG. 17.
Figure 20:
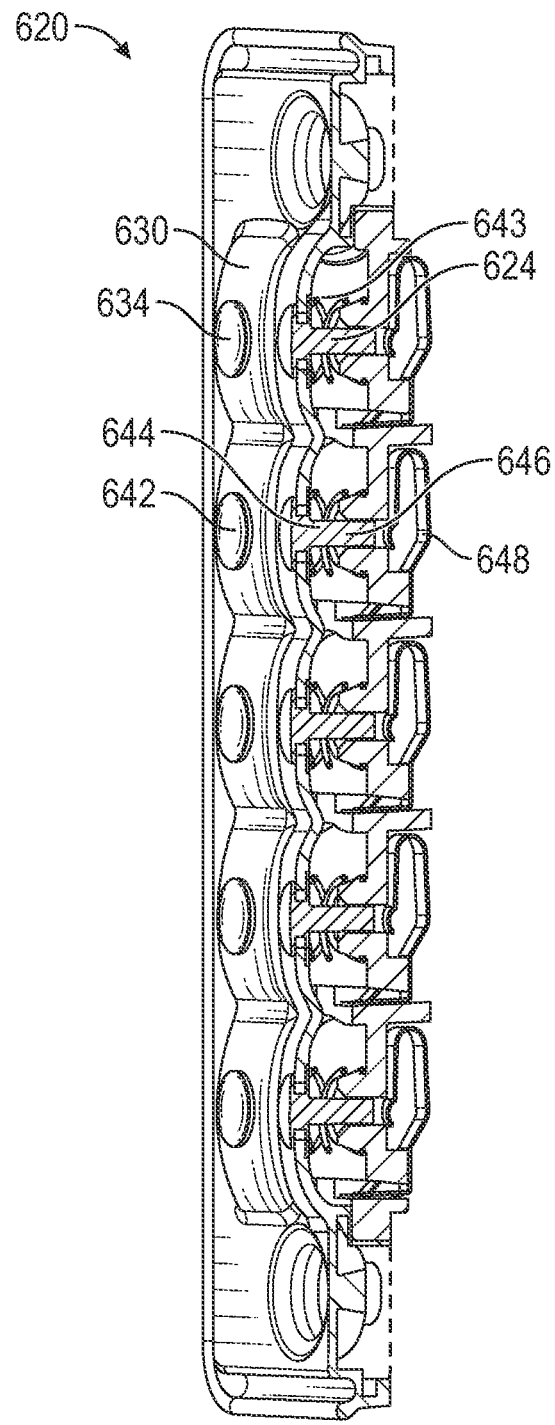
FIG. 20 is a cross-sectional perspective view of the electrical connector of FIG. 17.
Figure 21:
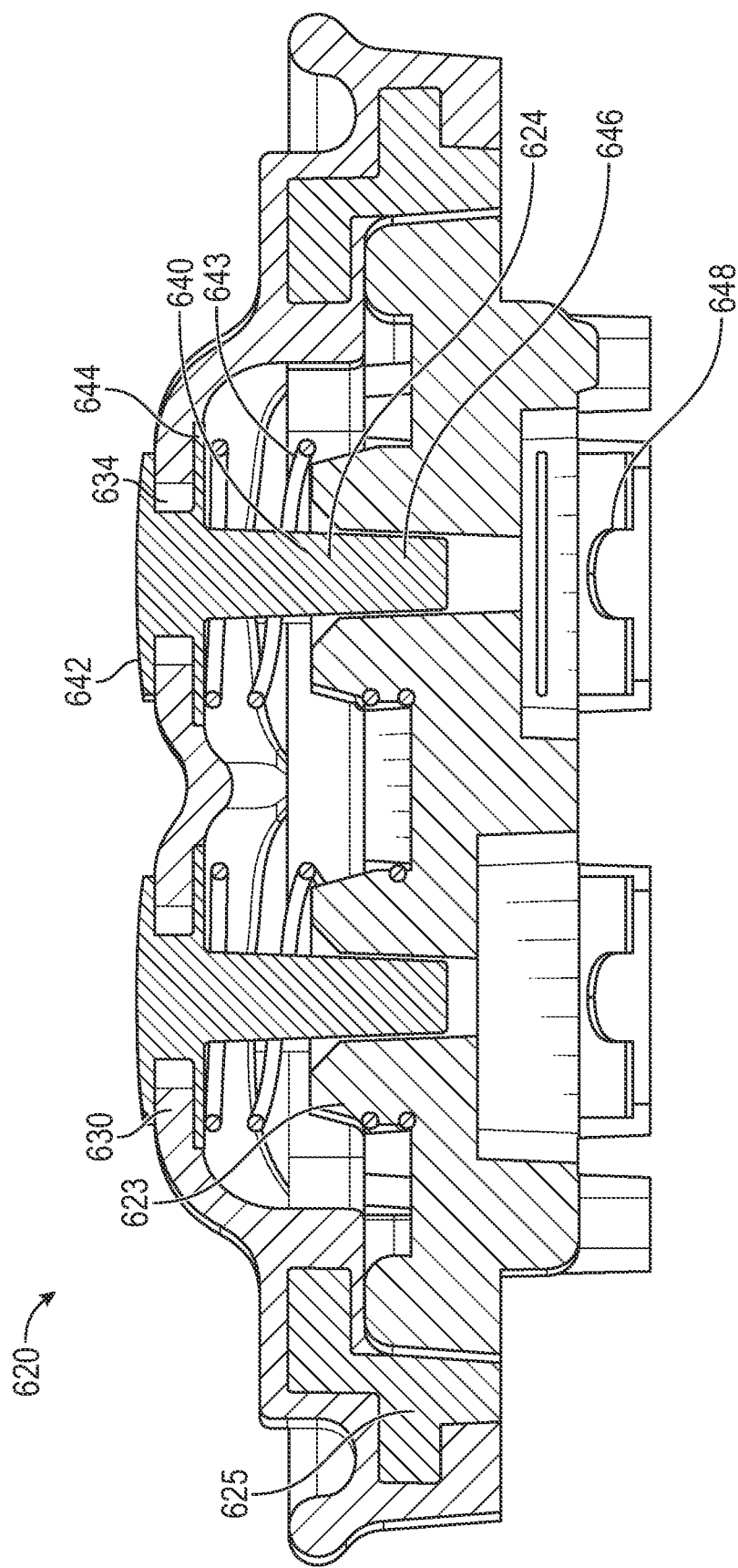
FIG. 21 is a detail cross-sectional view of the electrical connector of FIG. 17.

FIG. 18 is a bottom view of the electrical connector 620 of FIG. 17. FIG. 19 is a cross-sectional view of the electrical connector 620 of FIG. 17. FIG. 20 is a cross-sectional perspective view of the electrical connector 620 of FIG. 17. FIG. 21 is a detail cross-sectional view of the electrical connector 620 of FIG. 17. With reference to FIGS. 17-21, the connector pins 624 can be secured within the electrical connector 620.

In the depicted example, the radial seal 630 can interface with features of the connector pins 624 to retain the connector pins 624 within the radial seal 630 and the electrical connector 620 to prevent pullout of the connector pins 624. For example, an upper contact head 642 and a lower contact head 644 can each radially extend from the stud 646 of the connector pin 624 to engage with the radial seal 630. In some embodiments, the upper contact head 642 and the lower contact head 644 can be spaced apart to capture a portion of the radial seal 630 there between, retaining the connector pin 624 within the radial seal 630. Optionally, the upper contact head 642 and/or lower contact head 644 can be larger than the respective aperture 634 of the radial seal 630 to prevent pullout of the connector pin 624. In some embodiments, the lower contact head 644 can be larger than the upper contact head 642.

As can be appreciated, the connector pins 624 can be inserted into the radial seal 630 from the inner face of the radial seal 630. In some embodiments, the apertures 634 can elastically stretch to allow the upper contact head 642 to pass through the aperture 634.

In the depicted example, when the connector pins 624 are mechanically engaged with a mating connector, the upper contact head 642 is displaced to move the stud 646 downward into contact with the contact spring 648 to allow for electrical signals to pass from the connector pin 624 and into the device. In some embodiments, the spring frame 625 can include a compression stop 623 to limit the downward travel or compression of the connector pin 624 to prevent damage to the electrical connector 620. The compression stop 623 can be molded into the spring frame 625. In some embodiments, the spring frame 625 can be supported by the housing of the functional module.

As can be appreciated, the connector pins 624 can be biased or urged upward to space apart the stud 646 from the contact spring 648. For example, a biasing spring 643 can bias or urge the connector pin 624 upward away from the contact spring 648. The biasing spring 643 can engage against the lower contact head 644. When the connector pin 624 is engaged with a mating connector, the biasing spring 643 can be compressed.

The various connector pins 624 can have different or staggered heights. In some embodiments, the length of the studs 646 of each connector pin 624 can be varied to adjust the height of the connector pin 624. By staggering the heights of the connector pins 624, the order of connection of the connector pins 624 can be controlled. For example, the longest pin 624 can come into contact with a mating connector before a shorter connector pin 624. Similarly, during disconnection, a shorter connector pin 624 can be disconnected before a longer connector pin 624 is disconnected. By altering the heights of the connector pins 524, certain functions or connections can be made active upon connection or remain active until the end of disconnection.

As can be appreciated, the connection pins 624, the biasing spring the contact spring 648, and PCB spacers can be formed or coated with conductive materials such as copper, nickel, and/or gold.

Figure 22:
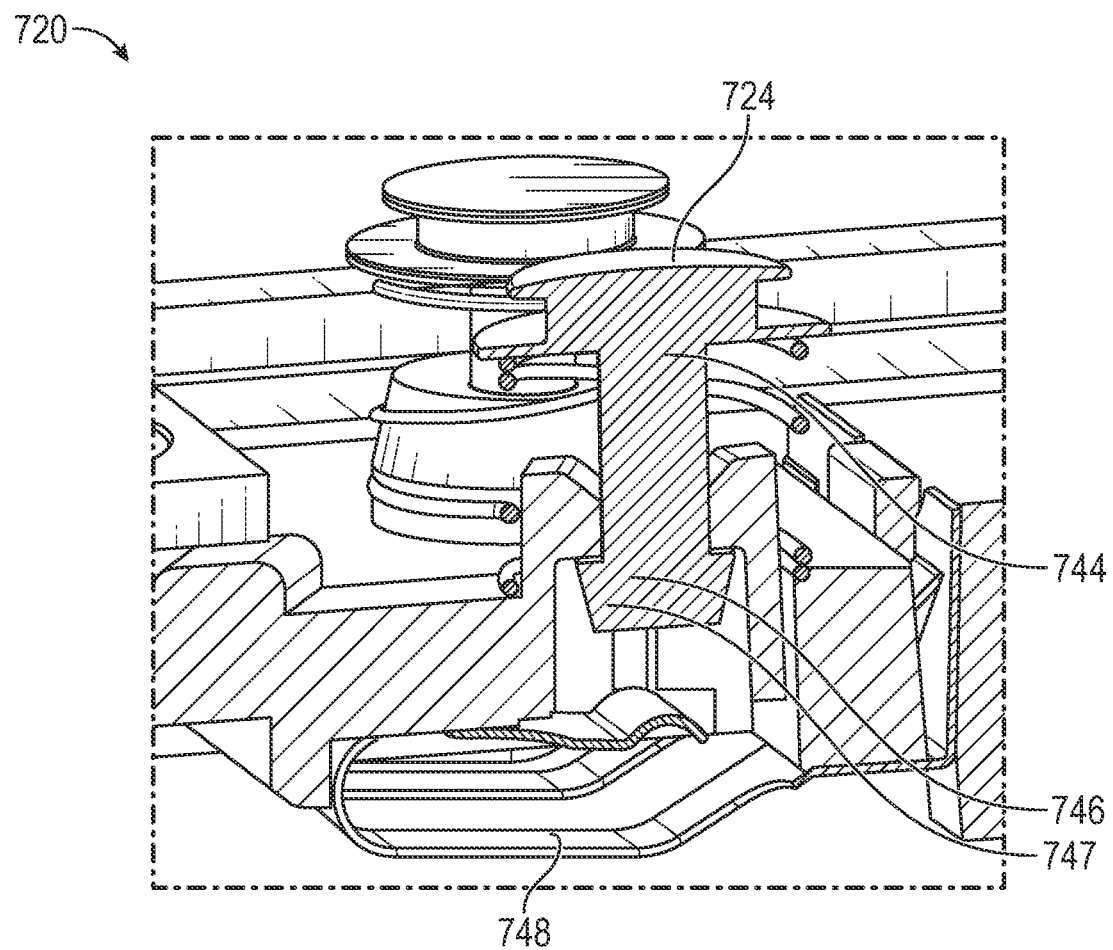
FIG. 22 is a detail cross-sectional perspective view of an electrical connector for a module of a patient care system, in accordance with some embodiments.

FIG. 22 is a detail cross-sectional perspective view of an electrical connector 720 for a module of a patient care system, in accordance with some embodiments. In the depicted example, the electrical connector 720 can include connector pins 724 that are locked into place to prevent the removal of the electrical contact. In some embodiments, the connector pin 724 can include a barbed interface 747 at a lower portion of the stud 746. When the connector pin 724 is displaced or lowered, the barbed interface 747 of the stud 746 can engage with a contact spring 748 to flex and displace the contact spring 748, latching the connector pin 724 into the contacted or lowered position. As illustrated, the barbed interface 747 can radially extend from the stud 746 and can include a conical shape.

Figure 23:
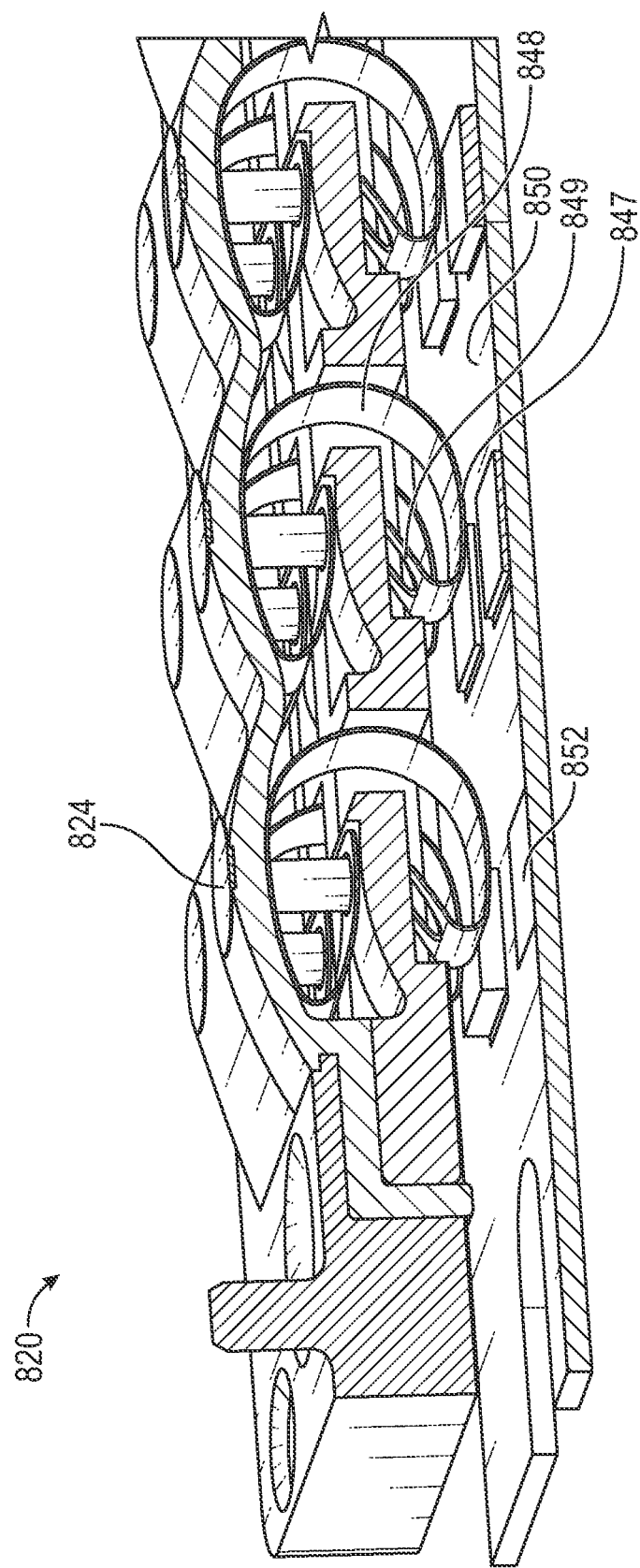
FIG. 23 is a detail cross-sectional perspective view of an electrical connector for a module of a patient care system, in accordance with some embodiments.

FIG. 23 is a detail cross-sectional perspective view of an electrical connector 820 for a module of a patient care system, in accordance with some embodiments. As described, the contact spring 848 facilitates electrical contact from the connector pin 824 to the PCB 850 of the functional module.

In a resting position, the connector pin 824 and the contact spring 848 are spaced apart from the PCB 850 and the PCB spacer 852. In the resting position, no electrical connection is made between the connector pin 824 and the PCB 850. In some embodiments, the contact spring 848 biases or urges the connector pin 824 upward away from the PCB 850.

Upon engagement with a mating connector, the connector pins 824 can be displaced or otherwise moved downward. By moving the connector pin 824 downward, the contact spring 848 can be moved downward to engage with the PCB spacer 852 of the PCB 850, facilitating an electrical connection between the contact head of the connector pin 824 and the PCB 850 of the module. In some embodiments, the compliance of the contact spring 848 can be configured to allow for contact with a desired engagement force without damaging the PCB spacer 852. In some embodiments, the contact spring 848 can have a reduced thickness compared to conventional contact springs, providing for reduced spring or biasing force.

In some embodiments, the contact spring 848 can include dual contact points at either the PCB contact portion 847 and/or the spring frame contact portion 849. Advantageously, by providing for dual (or multiple) contact points, the contact spring 848 can provide reliable contact and contamination tolerance.

Figure 24:
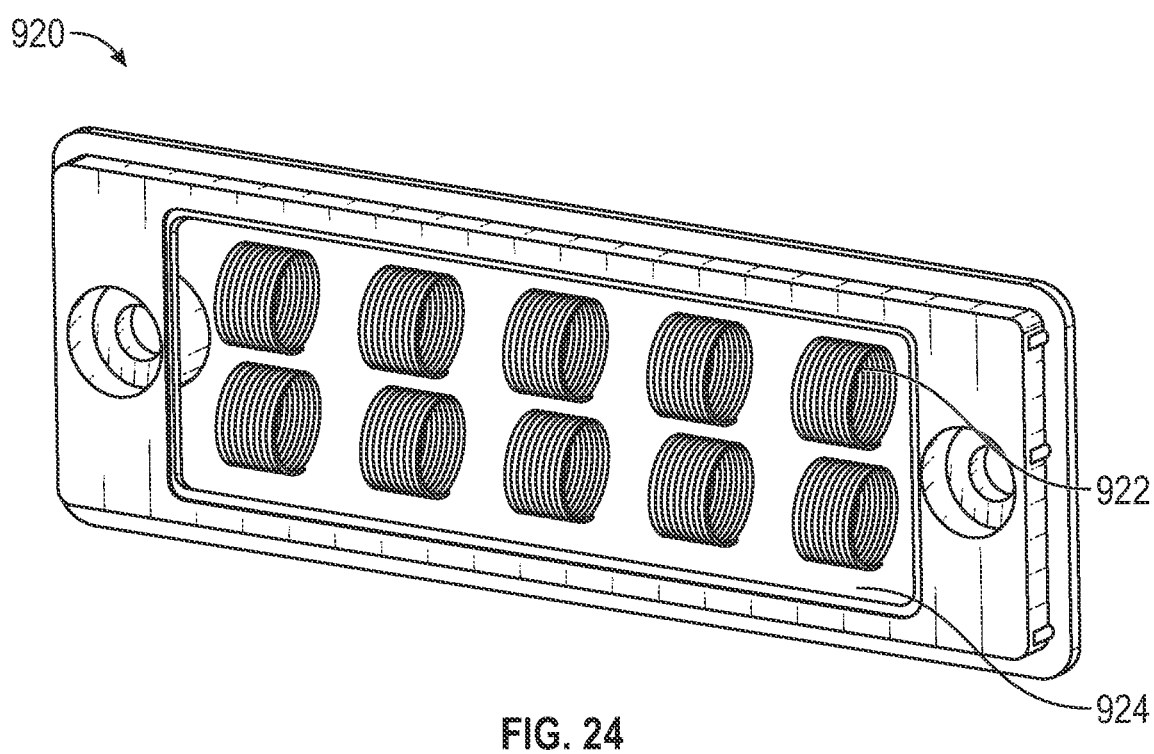
FIG. 24 is a perspective view of an electrical connector for a module of a patient care system, in accordance with some embodiments.

FIG. 24 is a perspective view of an electrical connector 920 for a module of a patient care system, in accordance with some embodiments. In the depicted example, the electrical connector 920 includes a plurality of connector coils 924 disposed along the connector face 922. The connector coils 924 can be configured to be in meshed engagement with mating connector coils. Advantageously, by providing a meshed engagement, the connector coils 924 can have a large surface contact, enhancing current capacity, life expectancy, and vibration tolerance of the electrical connector 920.

In the depicted example, the connector coils 924 are disposed radially extending away from the connector face 922. In some embodiments, the connector coils 924 are affixed in circumferential contact with the connector face 922. In some embodiments, the connector coils 924 extend radially through the connector face 922.

In some embodiments, the connector coils 924 are wound with conductive wire. The conductive wire can be wound with a pitch that allows a mating connector coil 924 to overlap and conduct electricity. The pitch of the connector coils 924 can be configured to provide a sufficient mating force. As can be appreciated, the wire diameter, length, and shape of the connector coil 924 can be configured for various applications. In some embodiments, the connector coil 924 can include a conductive plating. The electrical connector 920 can include an elastomeric covering, which may partially cover and/or retain the connector coils 924.

Figure 25:
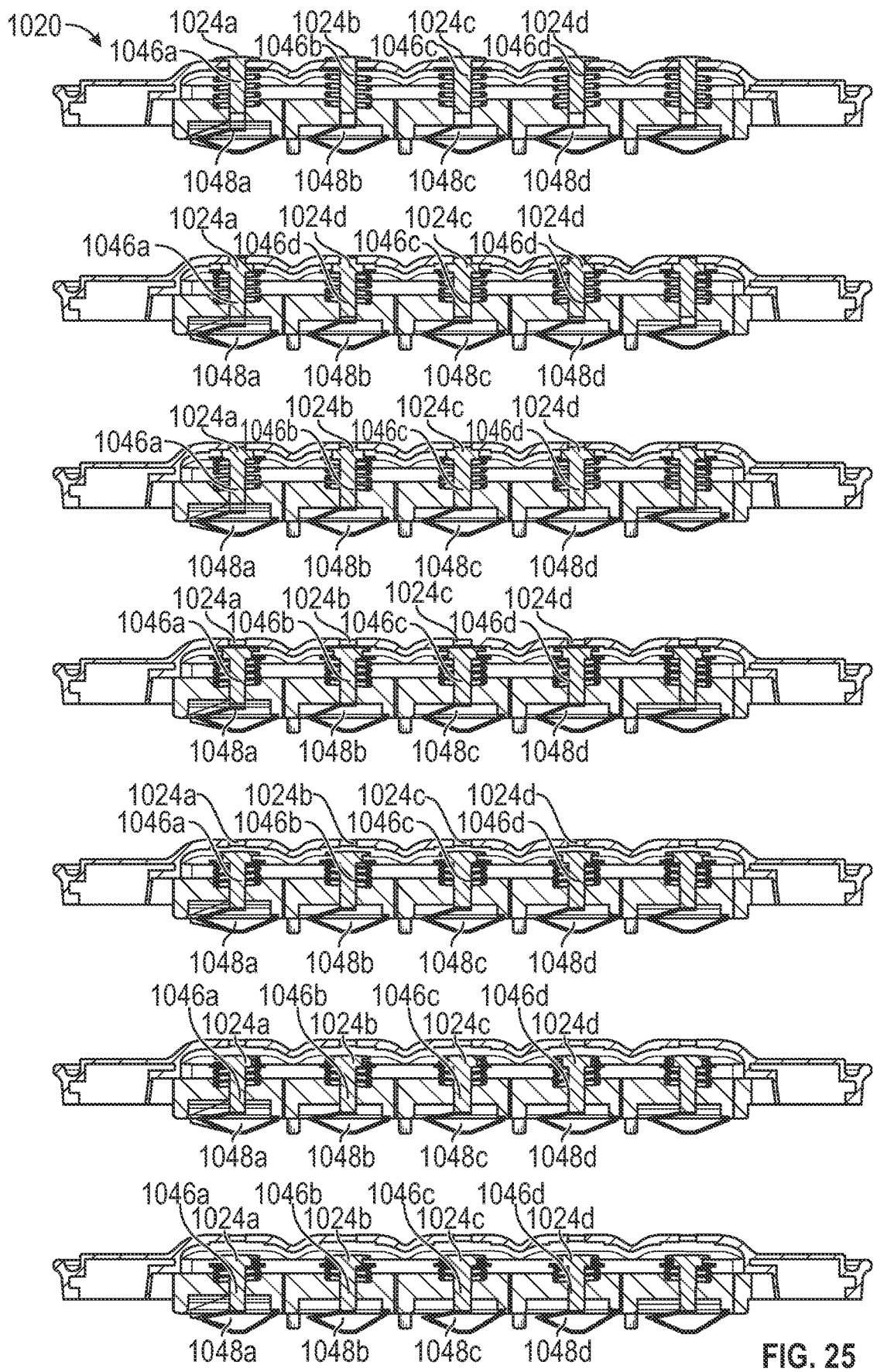
FIG. 25 is a plurality of cross-sectional views of an electrical connector for a module of a patient case system, in accordance with some embodiments.

FIG. 25 is a plurality of cross-sectional views of an electrical connector 1020 for a module of a patient case system, in accordance with some embodiments. In the depicted example, the electrical connector 1020 can be configured to control the order of connection and disconnection of various circuits terminated by the electrical connector 1020. As can be appreciated, the electrical connectors described herein can be configured in a similar manner.

In some embodiments, the various connector pins 1024a, 1024b, 1024c, 1024d can engage with respective contact springs 1048a, 1048b, 1048c, 1048d. In the depicted example, the contact springs 1048a, 1048b, 1048c, 1048d can have different or staggered heights relative to the respective connector pins 1024a, 1024b, 1024c, 1024d. By staggering the heights of the contact springs 1048a, 1048b, 1048c, 1048d, the order of connection of the connector pins 1024a, 1024b, 1024c, 1024d can be controlled. For example, the tallest contact spring 1048c can come into contact with the respective connector pin 1024c before a shorter contact spring and connector pin. Similarly, during disconnection, a shorter contact spring 1048a can be disconnected before a taller contact spring 1048c is disconnected. By altering the heights of the contact springs 1048a, 1048b, 1048c, 1048d, certain functions or connections can be made active upon connection or remain active until the end of disconnection.

For example, the tallest contact spring 1048c can be coupled to a ground channel, the next tallest contact spring 1048b can be coupled to a power channel, the next tallest contact spring 1048d can be coupled to a CAN channel, and the shortest contact spring 1048a can be coupled to a module channel. Therefore, as illustrated, during connection, the ground channel connector pin 1024c can be electrically connected first, the power channel connector pin 1024b can be coupled next, the CAN channel connector pin 1024d can be coupled next, and the module channel connector pin 1024a can be coupled last. Similarly, during disconnection, the channels can be disconnected in reverse order.

In some embodiments, the various connector pins 1024a, 1024b, 1024c, 1024d can have different or staggered heights. In some embodiments, the length of the studs 1046a, 1046b, 1046c, 1046d of each connector pins 1024a, 1024b, 1024c, 1024d can be varied to adjust the height of the connector pins 1024a, 1024b, 1024c, 1024d, controlling the order of connection of the respective channels.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

Various examples of aspects of the disclosure are described below as clauses for convenience. These are provided as examples, and do not limit the subject technology.

Clause 1. A module for a patient care system, the module comprising: a housing having an attachment side configured to releasably attach to an adjacent electronic module; a latch mechanism configured to engage a catch member on the adjacent electronic module to secure the attachment side to the adjacent electronic module; an electrical connector positioned on the attachment side and configured to electrically connect to an adjacent electrical connector on the adjacent electronic module; and a sensor coupled to the housing and configured to detect movement of the latch mechanism.

Clause 2. The module of Clause 1, wherein the latch mechanism includes a rotatable latch body.

Clause 3. The module of Clause 2, wherein the sensor is configured to detect rotation of the latch body.

Clause 4. The module of Clause 1, wherein the latch mechanism includes a translatable latch body.

Clause 5. The module of Clause 4, wherein the sensor is configured to detect translation of the latch body.

Clause 6. The module of Clause 1, wherein the latch mechanism includes a latch body configured to rotate and translate.

Clause 7. The module of Clause 6, wherein the sensor is omni-directional and is configured to detect rotation and translation of the latch body.

Clause 8. The module of Clause 1, wherein the sensor comprises a hall effect sensor.

Clause 9. The module of Clause 1, wherein the sensor comprises an optical interrupt sensor.

Clause 10. The module of Clause 1, wherein the sensor comprises a capacitance sensor.

Clause 11. The module of Clause 1, wherein the sensor comprises an inductance sensor.

Clause 12. A module for a patient care system, the module comprising: a housing having an attachment side configured to releasably attach to an adjacent electronic module; and an electrical connector positioned on the attachment side and configured to electrically connect to an adjacent electrical connector on the adjacent electronic module.

Clause 13. The module of Clause 12, wherein the electrical connector includes an elastomeric seal.

Clause 14. The module of Clause 13, wherein the elastomeric seal comprises a radial seal.

Clause 15. The module of Clause 13, wherein the elastomeric seal comprises an axial seal.

Clause 16. The module of Clause 12, wherein the electrical connector comprises a plurality of connector pins.

Clause 17. The module of Clause 16, wherein at least one of connector pins of the plurality of connector pins is retained by a seal.

Clause 18. The module of Clause 16, further comprising a plurality of contact springs spaced apart from the plurality of connector pins, wherein the plurality of connector pins are configured to contact the plurality of contact springs.

Clause 19. The module of Clause 18, wherein a first contact spring of the plurality of contact springs has a first height and a second contact spring of the plurality of contact springs has a second height, the first height being different than the second height.

Clause 20. The module of Clause 16, wherein a first connector pin of the plurality of connector pins has a first height and a second connector pin of the plurality of connector pins has a second height, the first height being different than the second height.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

What is claimed is:

1. A module for a patient care system, the module comprising:
   an electrical connector configured to electrically connect to an adjacent electrical connector on an adjacent electronic module, wherein the electrical connector comprises:
   a radial elastomeric seal defining a plurality of apertures;
   a plurality of connector pins, wherein each connector pin comprises an engagement feature configured to retain the connector pin within a respective aperture of radial elastomeric seal; and
   a plurality of contact springs spaced apart from the plurality of connector pins, wherein the plurality of connector pins are configured to contact the plurality of contact springs.

2. The module of claim 1, wherein a first connector pin of the plurality of connector pins has a first height and a second connector pin of the plurality of connector pins has a second height, the first height being different than the second height.

3. The module of claim 1, wherein a first contact spring of the plurality of contact springs has a first height and a second contact spring of the plurality of contact springs has a second height, the first height being different than the second height.

4. The module of claim 1, wherein the engagement feature comprises an upper contact head and a lower contact head spaced apart from the upper contact head.

5. The module of claim 4, wherein the upper contact head and the lower contact head are configured to capture a portion of the radial elastomeric seal therebetween.

6. The module of claim 4, wherein the upper contact head and the lower contact head are configured to prevent pullout of the respective connector pin.

7. The module of claim 4, wherein the upper contact head and the lower contact head each extend from a stud of the connector pin.

8. The module of claim 4, wherein the upper contact head is larger than the respective aperture of the radial elastomeric seal.

9. The module of claim 8, wherein the lower contact head is larger than the respective aperture of the radial elastomeric seal.

10. The module of claim 9, wherein the lower contact head is larger than the upper contact head.

11. A module for a patient care system, the module comprising:
    an electrical connector configured to electrically connect to an adjacent electrical connector on an adjacent electronic module, wherein the electrical connector comprises:
    a plurality of connector pins, wherein each connector pin comprises a barbed interface; and
    a plurality of contact springs spaced apart from the plurality of connector pins, wherein the plurality of connector pins are configured to contact the plurality of contact springs, wherein the barbed interface is configured to engage with a respective contact spring to latch the respective connector pin in a lowered position.

12. The module of claim 11, wherein the barbed interface radially extends from a stud of the connector pin.

13. The module of claim 11, wherein the barbed interface comprises a conical shape.

14. The module of claim 11, wherein a first contact spring of the plurality of contact springs has a first height and a second contact spring of the plurality of contact springs has a second height, the first height being different than the second height.

15. A module for a patient care system, the module comprising:
- an electrical connector configured to electrically connect to an adjacent electrical connector on an adjacent electronic module, wherein the electrical connector comprises:
a connector face; and
- a plurality of connector coils, wherein each connector coil is disposed along the connector face and is configured to provide meshed engagement with a mating connector coil.

16. The module of claim 15, wherein each connector coil is disposed radially extending away from the connector face.

17. The module of claim 15, wherein each connector coil is affixed in circumferential contact with the connector face.

18. The module of claim 15, wherein each connector coil extends radially though the connector face.

19. The module of claim 15, wherein each connector coil comprises an elastomeric covering.

* * * * *